United States Patent [19]

Anselem et al.

[11] Patent Number: 5,716,637

[45] Date of Patent: *Feb. 10, 1998

[54] SOLID FAT NANOEMULSIONS AS VACCINE DELIVERY VEHICLES

[75] Inventors: Shimon Anselem, Rehovot, Israel; George H. Lowell, Baltimore, Md.; Haim Aviv, Rehovot; Doron Friedman, Carmei Yosef, both of Israel

[73] Assignees: Pharmos Corporation, New York, N.Y.; The United States of America as represented by the Secretary of the Army, Washington, D.C.

[*] Notice: The term of this patent shall not extend beyond the expiration date of Pat. No. 5,576,016.

[21] Appl. No.: 553,350

[22] PCT Filed: May 18, 1994

[86] PCT No.: PCT/US94/05589

§ 371 Date: Nov. 16, 1995

§ 102(e) Date: Nov. 16, 1995

[87] PCT Pub. No.: WO94/26255

PCT Pub. Date: Nov. 24, 1994

Related U.S. Application Data

[63] Continuation-in-part of Ser. No. 63,613, May 18, 1993, Pat. No. 5,576,016.

[51] Int. Cl.$^6$ .............................. A61K 9/127; A61K 9/16
[52] U.S. Cl. .................... 424/450; 424/489; 424/490; 424/502; 424/184.1; 424/188.1; 424/204.1; 424/208.1; 424/234.1; 424/237.1; 424/236.1; 424/269.1; 428/937; 514/937
[58] Field of Search ........................ 424/450, 489, 424/490, 497, 45, 427, 502, 184.1, 188.1, 204.1, 208.1, 234.1, 237.1, 236.1, 269.1; 514/937–943; 428/402.2

[56] References Cited

U.S. PATENT DOCUMENTS

| | | | |
|---|---|---|---|
| 4,880,635 | 11/1989 | Janoff | 424/450 |
| 5,023,271 | 6/1991 | Vigne | 514/458 |
| 5,171,737 | 12/1992 | Weiner | 514/3 |
| 5,188,837 | 2/1993 | Domb | 424/450 |
| 5,284,663 | 2/1994 | Speaker | 424/489 |
| 5,302,401 | 4/1994 | Livesidge | 424/489 |
| 5,306,508 | 4/1994 | Kossovsky | 424/493 |
| 5,308,624 | 5/1994 | Maircent | 424/427 |
| 5,576,016 | 11/1996 | Amselem | 424/450 |

FOREIGN PATENT DOCUMENTS

| | | |
|---|---|---|
| 0 315 079 | 5/1989 | European Pat. Off. . |
| 0 506 197 | 9/1992 | European Pat. Off. . |
| WO91/07171 | 5/1991 | WIPO . |

OTHER PUBLICATIONS

CRC Press, Inc., Liposome Technology, 2nd Edition, vol. 1, Chapter 28, p. 501, Liposome Preparation and Related Techniques, edited by Gregory Gregoiadis, Ph.D., "A Large–Scale Method For the Preparation Of Sterile And Nonpyrogenic Liposomal Formulations Of Defined Size Distributions For Clinical Use", Shimon Amselem, Alberto Gabizon, and Yechezkel Barenholz.

(List continued on next page.)

*Primary Examiner*—Gollamudi S. Kishore
*Attorney, Agent, or Firm*—Pennie & Edmonds

[57] ABSTRACT

The present invention provides pharmaceutical vaccine compositions that are nanoemulsions of particles having a lipid core which is in a solid or liquid crystalline phase at 25° C., and which is surrounded by at least one phospholipid bilayer for the parenteral, oral, intranasal, rectal, vaginal or topical delivery of both hydrophilic and lipophilic immunogens. The particles have a mean diameter in the range of 10 to 250 nm and the immunogen is incorporated therein, either intrinsically prior to the homogenization process or extrinsically thereafter.

44 Claims, 8 Drawing Sheets

OTHER PUBLICATIONS

Methods of Biochemical Analysis, vol. 33, D. Glick, editor, J. Wiley & Sons, N.Y., 1988, "Liposomes: Preparation, Characterization, and Preservation", Dov Lichtenberg and Yechezkel Barenholz.

Journal of Pharmaceutical Sciences, vol. 79, No. 12, Dec. 1990, "optimization and Upscaling of Doxorubicin–Containing Liposomes for Clinical Use", S. Amselem, A. Gabizon and Y. Barenholz.

CRC Press, Inc., 1993, Liposome Technology, 2nd Ed., edited by G. Gregoriadis, Ph.D., vol. 1, Chapter 3, p. 49, "Liposome Preparation Using High–Pressure Homogenizers", Martin M. Brandi, Bieter Bachmann, Markus Drechsler, and Kurt H. Bauer.

Elsevier Science Publishers B.V. (Biomedical Division, 1986, Laboratory Techniques in Biochemistry and Molecular Biology, vol. 3, part 2, edited by R.H. Burdon and P.H. van Knippenbert, "Techniques of Lipidology — Isolation, Analysis and Identification of Lipids", 2nd revision edition, Moris Kates.

Prog. Lipd Res., vol. 31, No. 4 pp. 345–372, 1992, "Recent Aspects in the Use Of Liposomes in Biotechnology and Medicine" by Toshinori Sato et al.

Vol. 6, p. 195, "Liposomes As Carrier for Vaccines" by Carl R. Alving — Walter Reed Army Institute of Research, Washinton, D.C.

American Chemical Society, vol. 18, No. 19, 1979, p. 4169, "Dependence of the Conformation of the Polar Head Groups of Phosphatidycholine on Its Packing in Bilayers. Nuclear Magnetic Resonance Studies on the Effect of the Binding of Lanthanide Ions" by Dov Lichtenberg et al.

Proc. Natl. Acad. Sci. USA, vol. 89, pp. 358–362, Jan. 1992, Immunology — "Liposomal malaria vaccine in humans: A safe and potent adjuvant strategy" by Louis F. Fries et al.

FIG. 6

SOLID FAT NANOEMULSIONS AS VACCINE DELIVERY VEHICLES

CROSS-REFERENCE TO RELATED APPLICATION

The present application 371 of PCT/US94/05589 filed May 18, 1994, published as WO94/26255 Nov. 24, 1994, is a continuation-in-part of U.S. patent application Ser. No. 08/063,613, filed May 18, 1993 now U.S. Pat No. 5,576,016.

FIELD OF THE INVENTION

The present invention concerns methods and compositions for delivery of vaccines by parenteral and other routes of administration. More particularly, it concerns stable lipid-in-water nanoemulsions or emulsomes containing small lipid particles which are useful as delivery vehicles for both hydrophilic and lipophilic immunogens enhancing their immunogenicity and improving their immune response.

BACKGROUND OF THE INVENTION

The body's immune system recognizes pathogens as foreign and is thought to produce antibodies to them by two main pathways. In one pathway, antigens on the pathogen surface presumably bind to receptor molecules on the white blood cells known as B cells, causing them to become plasma cells, which proliferate and secrete antibodies specific for the pathogen. In the second pathway, circulating macrophages bind to the pathogens, endocytose them, and display processed antigens on their surface.

T cells then bind to the expressed antigen and by way of several complex steps this binding ultimately results in further plasma cell proliferation and increased antibody production.

In the past, the risks of whole-pathogen vaccines and limited supplies of useful antigens posed barriers to development of practical vaccines. Today, the tremendous advances of genetic engineering and the ability to obtain many synthetic recombinant protein antigens derived from parasites, viruses, and bacteria has revolutionized the development of new generation vaccines.

Although the new, small synthetic antigens offer advantages in the selection of antigenic epitopes and safety, a general drawback of small antigens is poor immunogenicity.

Unfortunately, the body's immune system does not respond strongly to small peptides. In particular, macrophages do not readily ingest and process the small antigens resulting in low antibody titers and the need for repeated immunizations. This lack of immunogenicity has created an acute need to identify pharmaceutically acceptable delivery systems for these new antigens.

Several reports describing the improvement of immune response achieved by the association of antigens with lipid carriers such as liposomes or microparticles like polymeric biodegradable microcapsules have been published (C. R. Alving, *Liposomes as Carriers of Vaccines*, in "Liposomes: From Biophysics to Therapeutics", M. J. Ostro, ed., Ch. 6, Marcel Dekker Inc., New York, 1987, pp. 195–218; J. H. Eldridge et al, *Molec. Immunol.*, 28, 287, 1991). The ability of these delivery systems to enhance immunogenicity was related to the physicochemical characteristics of the particles.

When antigens are incorporated in lipid carriers by encapsulation or entrapment, or embedded in their surface, they show enhanced ability to evoke a strong immune response. Vaccines formulated in lipid carriers probably enhance antibody production by increasing activity along both pathways of stimulation of immune system described above. When multiple antigens attached to a lipid carrier bind to multiple receptors on a B cell, the resulting plasma cell probably proliferates faster than it does when it encounters a solitary antigen. Similarly, whereas a macrophage is unlikely to phagocytase a small antigen efficiently, it will readily digest a lipid carrier particle containing the antigen. When phagocytosis takes place, antigens coupled to the surface of the lipid carrier or encapsulated within the particle are ingested and possibly displayed as processed antigen on the macrophage surface. Such antigen presentation could result in T cell activation and additional plasma cell proliferation and increased antibody production.

Most vaccine adjuvants are also surface-active, or have a special surface interface. Surface-active agents concentrate at the surface formed by the interface of water and non-polar substances such as lipid or lipid membrane. Most adjuvants are also water-insoluble surfactants, so lipoidal vehicles are necessary for proper delivery of the antigen.

The use of liposomes as drug delivery systems has been known for some time, and comprehensive review articles on their properties and clinical applications are available; see, e.g., Barenholz and Amselem, in "*Liposome Technology*", 2nd ed., G. Gregoriadis, ed., CRC Press, 1992; Lichtenberg and Barenholz, in *Methods for Biochemical Analysis*, 33, D. Glick, ed., 1988. A liposome is defined as a structure consisting of one or more concentric lipid bilayers separated by water or aqueous buffer compartments. These hollow structures, which have an internal aqueous compartment, can be prepared with diameters ranging from 20 nm to 10 µm. They are classified according to their final size and preparation method as: SUV, small unilamellar vesicles (0.5–50 nm); LUV, large unilamellar vesicles (100 nm); REV, reverse phase evaporation vesicles (0.5 µm); and MLV, large multilamellar vesicles (2–10 µm).

An extensive literature exists on immunologic characteristics of liposomes, and numerous reviews on their potential as vaccine carriers have been published especially by C. R. Alving and co-workers who developed the first injectable liposomal vaccine for human use administered to 30 volunteers in a Phase I study (Fries et al, *Proc. Natl. Acad. Sci. USA*, 89, pp. 358–362, 1992).

Emulsions are defined as heterogeneous systems of one liquid dispersed in another in the form of droplets usually exceeding 1 µm in diameter. The two liquids are immiscible and chemically unreactive or slowly reactive. An emulsion is a thermodynamically unstable dispersed system. Instability is a result of the system's tendency to reduce its free energy by separating the dispersed droplets into two liquid phases. Instability of an emulsion during storage is evidenced by creaming, flocculation (reversible aggregation), and/or coalescence (irreversible aggregation).

The use of parenteral emulsions as drug delivery systems is still comparatively rare because of the necessity of achieving stable microdroplets of less than 1 µm to prevent formation of emboli in the blood vessels. In order to increase the stability and useful lifetime of the emulsion, the dispersed lipid droplets must be coated or treated with surfactants or "stabilizers", which lower the free energy at the interface and decrease the tendency of droplets to coalesce. However, due to their detergent characteristics, most of them are hemolytic agents which act as membrane solubilizers, producing deleterious side effects upon injection into the body. Formulation options are severely restricted by the very limited selection of stabilizers and surfactants approved and safe for parenteral injection.

SUMMARY OF THE INVENTION

The present invention provides pharmaceutical compositions comprising nanoemulsions of particles comprising a lipid core composed of a lipid which is in a solid or liquid crystalline phase at at least 25° C., stabilized by at least one phospholipid envelope, for the parenteral, oral, ocular, rectal, vaginal, intranasal, or topical delivery of both fat-soluble and water-soluble immunogens. The new entity is a particulate vehicle which is denoted herein as a solid fat nanoemulsion or "emulsome." These compositions have features which are intermediate between liposomes and oil-in-water emulsions. Emulsome particles contain a hydrophobic core, as in standard oil-in-water emulsions, but surrounded and stabilized by one or more bilayers or envelopes of phospholipid molecules, as in liposomes (FIGS. 1A, 1B and 1C).

A key feature of these particles is that the core is composed of a lipid which in bulk form is in a solid or liquid crystalline phase, rather than an oil in a fluid phase. Lipid compositions of the core are characterized as being in the solid or liquid crystal phase at at least 25° C. when measured in bulk form.

Emulsomes, having the characteristics of both liposomes and emulsions, provide the advantages of high loading of hydrophobic bioactive compounds in the internal solid lipid core and the ability to encapsulate water-soluble antigens in the aqueous compartments of surrounding phospholipid layers.

The present pharmaceutically stable solid fat nanoemulsions or emulsomes may be formulated in the absence of any ionic or non-ionic nonnatural synthetic surfactants or cosurfactants such as polyoxamers, deoxycholate, polysorbates, tyloxapol, or emulphor. They are stabilized by the combination of relatively high lecithin content and the use of solid lipid compositions as the core.

The particle size distribution of emulsomes, based on differential weight percents, is in the range of 10–250 nm, making them suitable for parenteral administration.

The emulsome technology represents a new type of lipid-based encapsulation technology that has potential usefulness as carriers of vaccines and adjuvants enhancing the immunogenicity of antigens incorporated intrinsically or extrinsically into the particles.

Emulsome-vaccine formulations containing antigens can provide the surface interphase necessary for proper orientation of the adjuvant active material, resulting in enhanced antibody production and increased immune response. They seem to have the capability of concentrating the antigen and adjuvant on hydrophobic surfaces, where they are effectively presented to cells of the immune system.

Binding of antigen to a surface or presentation of a special type of surface for antigen adsorption, as in the case of emulsome-vaccines, appears to be critical for much of the biological activity of most agents reported as adjuvants. Therefore the emulsome technology can serve as effective vehicles or delivery systems for human and veterinary vaccines.

The use of emulsomes as a vaccine delivery system has other demonstrable advantages. Emulsomes of this invention provide effective pharmaceutical delivery for a broad variety of both water-soluble and water-insoluble immunogens with minimal local or systemic toxicity.

The hydrophobic core and surfactant provide a microenvironment which accommodates lipophilic immunogens such as lipid A or lipopolysaccharides as well as membrane-associated peptide antigen domains, while the aqueous continuous phase accommodates water-soluble peptide domains, or oligosaccharides.

The term "peptide" herein includes both oligopeptides and proteins. To facilitate intestinal uptake, the emulsions may be encapsulated in gelatin capsules or otherwise enterocoated to prevent their exposure to gastric fluids when the oral route of administration is selected.

Additional advantages of the emulsome technology for delivery of vaccines are: antigens and adjuvants can be incorporated simultaneously in the same formulation due to the hydrophilic-hydrophobic nature of the emulsome particles; high encapsulation efficiency of immunogens can be obtained; emulsomes can be formulated to act as depot for slow release of antigens avoiding the need for repeated vaccinations; the manufacturing technique of emulsomes is relatively simple and easy to scale-up.

The emulsome-vaccine formulations of this invention do not include any polyoxypropylene-polyoxyethylene block polymer, trehalose dimycolate, cell wall skeleton, or any immunostimulatory mycobacteria or muramyl peptide-like additives to be effective.

Another aspect of this invention is to provide compositions and methods for the preparation of emulsomes containing antigens, incorporated either intrinsically (emulsified together with the phospholipids and solid fat) or extrinsically (added externally to prepared emulsomes).

In some cases, the emulsomes of the present invention can be administered in combination with other adjuvant systems, such as proteosomes, as indicated in the examples.

The size, concentration and specific composition of emulsome vaccines may be varied to suit the particular antigen used. Moreover, such formulations may enhance both humoral and cell-mediated immunity (CMI) as do Freund's adjuvants. The emulsomes here described have been developed for human use and since their particles are of submicron size and contain no added pyrogenic moieties such as mycobacteria or muramyl-peptide derivatives they have, unlike Freund's adjuvants, great safety potential. They may be especially applicable to antigens that are vaccine candidates to protect against biologic toxins or infectious agents which have natural hydrophobic moieties as a component including transmembrane viral, bacterial or parasite proteins, membrane proteins such as proteosomes, lipopolysaccharides, glycolipids such as gangliosides, or a variety of proteins or peptides to which hydrophobic anchors have been chemically or genetically added.

In addition to parenteral vaccination, another aspect of this invention is to provide emulsome compositions and methods to achieve mucosal immunity by using emulsome preparations comprising a plurality of submicron particles, a mucoadhesive macromolecule, immunogenic peptide or antigen, and an aqueous continuous phase, which induces mucosal immunity by achieving mucoadhesion of the emulsome particles to mucosal surfaces. Mucous surfaces suitable for application of the emulsions of the present invention may include ocular (corneal, conjunctival), oral (buccal, sublingual), nasal, vaginal and rectal routes of administration.

BRIEF DESCRIPTION OF THE DRAWINGS

FIG. 6 is a graph showing enhanced lapine immunogenicity of SEB-Toxoid F antigen after parenteral immunization of rabbits with extrinsic emulsome vaccine compared to free antigen.

DETAILED DESCRIPTION OF THE INVENTION

Figure 1A:
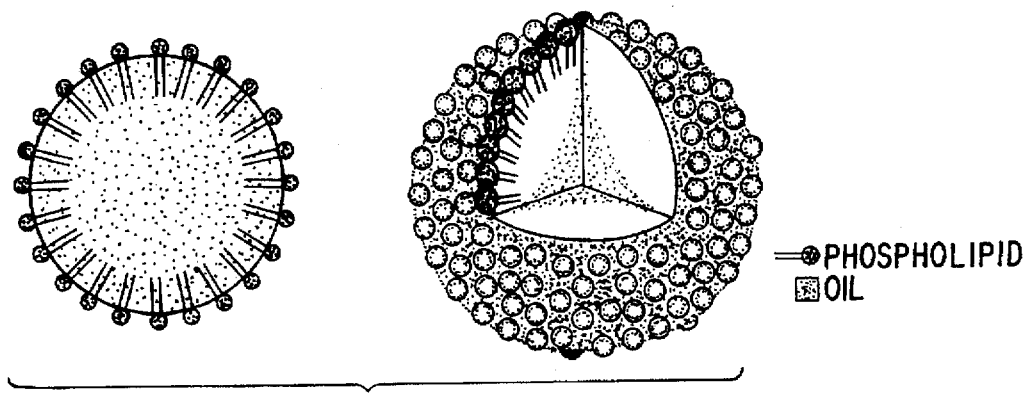
FIGS. 1A, 1B and 1C are schematic illustrations of a liposome, an oil-in-water submicron emulsion droplet, and a proposed structure for an emulsome particle, respectively.

This invention is directed to pharmaceutical compositions for the delivery of water-soluble and lipid-soluble vaccines, and to methods for preparing and using such compositions.

As used herein, the term "lipid" refers to compounds which are soluble in hydrocarbon solvents and are of a structural type which includes fatty acids and their esters, cholesterol and cholesteryl esters, and phospholipids.

The size range of emulsomes described in the present invention (10–250 nm) makes them suitable for parenteral delivery. The 10–250 nm range includes the mean size on a weight basis of preferred emulsome preparations. In more preferred preparations, the 10–250 nm size range includes at least 99% of the particles in the nanoemulsion, as determined on a weight basis. "Weight basis" determination as used herein means that the weight percent rather than the number of the lipid particles within the stated diameter range is used for the size determination. In certain preparations, the mean particle size plus or minus the standard deviation falls within the range 20 to 180 nm, 40 to 160 nm, or 50 to 150 nm. In other preparations, the mean and the standard deviation falls within the range 10 to 120 nm. In still more preferred preparations, 99% of the particles in the nanoemulsion fall within one of the above size ranges, as determined on a weight basis. All of the above emulsions can be sterilized by filtration.

Emulsomes can be administered parenterally, orally, topically, rectally, vaginally or intranasally.

Composition of the Lipid Core

An essential component of emulsomes is an internal hydrophobic or lipid core comprising a lipid which exhibits solid or liquid crystal or mixed solid and liquid crystal phases at room temperature (25° C.) when measured in bulk. The lipid may be a single compound or a mixture. The term "lipid" as applied to the lipid core herein may refer either to a single pure lipid compound or to a mixture of lipid compounds present in the core.

Lipid compositions suitable for use as the core component of emulsomes may be characterized as being in the solid or liquid crystalline phase at at least about 25° C., when measured in bulk form without incorporation into emulsomes. Some lipid compounds present in a mixture optionally may be fluids at 25° C. when pure, provided that the lipid mixture as a whole is solid or liquid crystalline in bulk at 25° C. In preferred compositions, at least 90% of the individual lipid compounds present in the core are solids or liquid crystals at 25° C. when measured in pure bulk form.

Phase determination preferably may be performed on the bulk lipid, i.e., a macroscopic sample of the same composition, prior to its incorporation into the emulsome core. The macroscopic phase determination on a bulk sample may be made on a melting apparatus or by spectroscopic means, such as IR, NMR, or fluorescence intensity or anisotropy. Bulk phase determination of an existing emulsome preparation may be performed by first extracting the core lipids, then measuring.

Lipids which form the lipid core are composed almost exclusively of nonpolar moieties which therefore do not exhibit a preference for the lipid-water interface. Triglycerides are the commonest type of fatty acid esters used in preparing the lipid core of nanoemulsions of this invention.

Triglycerides are a preferred material from which the lipid core may be prepared. The triglyceride core may be composed of a single pure triglyceride, usually available as a synthetic triglyceride, or may be a mixture of several triglycerides. Fats isolated from natural sources usually are available only as mixtures of triglycerides. Such natural mixtures are suitable for preparation of emulsomes, provided that the melting characteristics of the mixture are such that they exhibit a solid or liquid crystal phase at 25° C.

Detailed summaries of the phase behavior of various pure and mixed triglycerides are available; see D. Small, "Glycerides," in: *The Physical Chemistry of Lipids from Alkanes to Phospholipids*, Chapter 10, Plenum Press, New York, 1985; and M. Kates, *Techniques of Lipidology*, Chapter 1, North Holland, Amsterdam/American Elsevier Publ. Co., Inc., New York, 1972.

From the information available in these and other standard references, one skilled in the art may choose particular fats which have the requisite property of providing a solid or liquid crystal or mixed phase at 25° C. when measured in bulk. The melting properties of particular mixtures of fats may be determined readily by simple experiments.

Many triglycerides which are solid at 25° C. have fully saturated fatty acid chains. Saturated fatty acids are advantageous because they are incapable of undergoing peroxidation reactions, which lessen the acceptable storage life of oil-in-water emulsions.

Examples of solid fats suitable for the preparation of emulsomes are triglycerides composed of natural, even-numbered and unbranched fatty acids with chain lengths in the C10–C18 range, or microcrystalline glycerol triesters of saturated, even-numbered and unbranched fatty acids of natural origin such as tricaprin, trilaurin, trimyristin, tripalmitin, and tristearin. In general, any lipid component or mixture of lipid components which provides a solid phase at room temperature (25° C.) when measured in bulk is suitable for the lipid core.

Other preferred lipid core components are esters of monounsaturated fatty acids. Although monounsaturated fatty acids are capable of undergoing peroxidation, they are less reactive than typical polyunsaturated fatty acids. Natural monounsaturated fatty acids have the cis configuration. In general, these are lower melting than completely saturated fatty acid esters. Usually, therefore, monounsaturated fatty acid esters will be most useful in a mixture with higher melting saturated fatty acid esters.

Other triglycerides which are solid at 25° C. include partially hydrogenated vegetable oils. Unlike naturally occurring unsaturated fatty acids, hydrogenated oils contain unsaturated bonds in the trans configuration, which is higher melting than the cis configuration. Partially hydrogenated vegetable oils yield solid vegetable shortening (e.g., CRISCO), which may be used to prepare emulsomes which are free of cholesterol or cholesteryl esters.

Triglycerides containing polyunsaturated fatty acids may be present in small amounts in the lipid core of emulsomes, provided that the resulting triglyceride mixture is in the solid or liquid crystal phase at 25° C. when measured in bulk.

In some embodiments, the lipid of the hydrophobic core may have a solid to fluid phase transition (melting) temperature between 25° C. and physiological temperature (37° C.) when measured in bulk. For example, tricaprin melts at 35°–37° C., and is wholly or predominantly in the fluid phase at physiological temperature.

Tricaprin may be used to form an excellent lipid core for nanoemulsions. The lipid core alternatively may be composed of lipids which are in the solid phase at 37° C. when measured in bulk, such as higher saturated triglycerides, e.g., tripalmitin or tristearin.

Cores of mixed fluid and solid phases at 37° C. are also possible, particularly when the core contains mixtures of lipids.

The lipid or hydrophobic core of emulsomes also may be composed of or contain monoesters of fatty acids, such as waxes. In general, waxes are long chain fatty alcohol esters of fatty acids. Many waxes have suitable melting characteristics for use in emulsomes, since they are solids at 25° C. Examples include the esters from beeswax and spermaceti, such as cetyl palmitate.

Preferred waxes are made from saturated or monounsaturated fatty acids and saturated or unsaturated fatty alcohols. An example of the latter is provided by arachidyl oleate.

Other satisfactory monoesters include solid monoglycerides such as glyceryl monostearate, and fatty acid esters of short chain alcohols such as ethyl stearate.

Cholesterol and cholesteryl esters optionally may be incorporated into the lipid core or the surrounding phospholipid envelope. Cholesterol and its esters change the packing structure of lipids, and in high concentrations they induce the formation of a liquid crystal phase. A liquid crystal phase may co-exist with a solid phase under some conditions.

Preferred cholesteryl esters are those of saturated or monounsaturated long chain fatty acids, such as palmitoyl or oleoyl, respectively. Cholesteryl esters may be present in levels up to 50 mol % relative to the triglyceride or other solid lipid core component.

Since cholesterol has a polar alcohol group, it tends to incorporate into the envelope monolayers or bilayers rather than into the lipid core itself, and should be considered a component of the phospholipid envelope rather than of the core.

The lipid cores of emulsome particles of this invention optionally may contain one or more antioxidants. A preferred antioxidant is α-tocopherol or its derivatives, which are members of the Vitamin E family. Other antioxidants include butylated hydroxytoluene (BHT).

Antioxidants lessen the formation of oxidative degradation products of unsaturated lipids, such as peroxides. The need for antioxidants may be lessened by preparing the lipid core from saturated fatty acids.

Lipid particles of the invention preferably do not contain serum apolipoproteins such as apo B, apo AI, apo AII, or apo E. The apo B protein has the effect of targeting intravenously administered lipid particles to certain cellular receptors, such as the LDL receptor on hepatocytes and certain other cells.

Lipid particles of the invention preferably also are substantially free of intracellular marker proteins, such as those associated with the intracellular cytoskeleton (e.g., actin, myosin, troponin, tubulin, vimentin, spectrin).

Lipid particles which do not contain intracellular marker proteins or serum apolipoproteins are herein described as "noncellular" particles, since they lack characteristic indicia of lipid particles present in or derived from cellular sources.

In addition, preferred preparations of emulsomes are substantially free of lipase and phospholipase enzymatic activity. As defined herein, an emulsion is "substantially free" of lipase or phospholipase activity if the emulsion lipids or phospholipids are enzymatically cleaved at a rate of less than 0.1% per day when stored at room temperature.

In addition to immunogens, other natural, synthetic, or recombinant proteins and peptides optionally may be present in emulsomes. An example of natural protein is collagen, which may be used to prepare emulsomes with controlled or sustained release properties. This is described in greater detail below.

Surface Active Molecules

In lipid particles of the invention, the lipid core is surrounded by at least one envelope or layer containing phospholipid molecules. The phospholipid envelope functions as a stabilizer or surface-active agent at the lipid-water interface, thereby lowering the surface tension.

In preferred embodiments, phospholipid molecules comprise at least 90%, more preferably 95%, even more preferably at least 99% of the surface-active molecules covering the lipid core.

However, other surfactants may be used in small amounts, such as the non-natural nonionic surfactant TWEEN. The lipid core of the nanoemulsion particles may be covered or surrounded by more than one layer or envelope of surface-active molecules containing phospholipids.

In general, the surface-active phospholipid molecules are believed to form a monolayer around the lipid core of the particles, with the polar phospholipid head groups at the aqueous interface. However, particularly at higher molar ratios of phospholipid to core lipid, excess phospholipid may be available to form one or more roughly concentric bilayers which encapsulate the lipid core with its associated phospholipid monolayer. The number of bilayer envelopes is variable, and may include one, two, or many bilayers. These bilayer envelopes entrap one or more aqueous compartments which may be made to contain a water-soluble antigen by creating the lipid particles in the presence of an aqueous solution of that antigen.

Although the multiple concentric bilayer model of the structure of emulsomes is proposed because it accounts for the observed ability of the particles to carry high loads of both lipid-soluble and water-soluble antigens, the present invention does not depend upon and is not limited by the accuracy of the model.

Other geometric relationships between the lipid core and phospholipid molecules are possible which might explain the antigen carrying capacity of emulsomes of the present invention.

The preferred phospholipids which constitute the surrounding envelopes of emulsomes are natural phospholipids such as soybean lecithin, egg lecithin, phosphatidylglycerol, phosphatidylinositol, phosphatidyl-ethanolamine, phosphatidic acid, sphingomyelin, diphosphatidylglycerol, phosphatidylserine, phosphatidyl-choline, cardiolipin, etc.;

synthetic phospholipids such as dimyristoylphosphatidylcholine, dimyristoylphosphatidylglycerol, distearoylphosphatidylglycerol, dipalmitoylphosphatidylcholine, etc.; and hydrogenated or partially hydrogenated lecithins and phospholipids.

In preferred embodiments, phospholipids which form "normal" phases (i.e., ionic "head" groups facing to the external aqueous phase and lipophilic "tails" facing internally) under physiological conditions of pH and ionic strength comprise at least 50% of the total phospholipids, more preferably at least 75%, most preferably at least 90% on a molar basis. Examples of normal phase forming phospholipids are phosphatidyl-choline (lecithin), phosphatidylglycerol, and phosphatidylinositol. By contrast, phosphatidlyl-ethanolamine has a tendency to form reverse phases, with the polar head groups oriented internally and the lipophilic tails oriented outwardly. Reverse phases also may be formed by cardiolipin or phosphatidic acid in the presence of $Ca^{+2}$ ions; by phosphatidic acid at pH less than 3; and by phosphatidylserine at pH less than 4.

The phospholipid component may be either saturated or unsaturated, and may have a gel to fluid phase transition temperature either above or below 25° C. Egg or soy phosphatidylcholines (egg or soy PC) are examples of phospholipids with transition temperatures well below room temperature. Dimyristoyl phosphatidyl-choline (DMPC) has a transition temperature slightly below room temperature.

Dipalmitoyl and distearoyl phosphatidylcholines (DPPC and DSPC) are examples of phospholipids with transition temperatures well above room temperature, and in fact even above physiological temperature (37° C.). Acceptable emulsomes may be made with these and many other phospholipids.

In general, emulsomes prepared with phospholipids which are in the gel phase at 37° C. are expected to have more rigid bilayer envelopes and longer circulation time in plasma.

Emulsomes may be prepared with molar ratios of phospholipid to total lipid in the range of 0.1 to 0.75 (10 to 75 mol %), more usually 0.1 to 0.5 (10 to 50 mol %). The molar ratio of phospholipid to core lipid typically may be in the range of 0.1:1 to 2:1, usually 0.1:1 to 1:1, often 0.2:1 to 0.9:1, frequently 0.2:1 to 0.8:1, and commonly 0.25:1 to 0.6:1.

On a weight basis, the ratio of phospholipid to core lipid usually falls in the range 0.5:1 to 1.5:1, and frequently 0.6:1 to 1.2:1.

Non-natural surfactants and detergents optionally may be incorporated into emulsomes in small amounts. As used herein, the terms "nonnatural surfactants" or "detergents" include a wide variety of manmade molecules which form micelles in aqueous solution and contain both lipophilic and hydrophilic domains; however, phospholipids which belong to naturally occurring structural type are excluded from this definition, regardless of whether a particular phospholipid is obtained by synthesis or by isolation from natural sources. Examples of non-natural surfactants include the polysorbates ("TWEEN"), sodium dodecylsulfate (SDS), polyethoxylated castor oil ("CREMOPHOR"), NP-40, and numerous other synthetic molecules. In preferred embodiments, nonnatural surfactants comprise less than 10% (mol/mol) of the total surfactant, more preferably less than 5%, still more preferably less than 1%, and most preferably less than 0.1%. A significant advantage of emulsomes is that they may be prepared as a stable nanoemulsion in the essential absence of nonnatural surfactants. Even nonnatural surfactants which have been approved for parenteral administration are prone to cause toxic or undesirable side effects, whereas the phospholipid surfactants used in emulsomes are physiologically compatible.

In experiments to determine the effect of non-natural surfactants on emulsome structure, polysorbate (TWEEN-80) was added to an emulsome preparation at final concentrations of 0.1, 0.5, and 1% (w/v). The mean size of the resulting emulsome particles decreased from 225 nm in the absence of polysorbate to 120, 40, and 35 nm, respectively. Thus increasing concentrations of synthetic surfactants progressively decrease the particle size, and higher concentrations than those used are expected to result in formation of micelles (1–10 nm diameter).

Negatively charged lipid molecules such as oleic acid, or negatively charged phospholipids such as phosphatidylglycerol, phosphatidic acid, phosphatidylinositol and phosphatidylserine, can be added to the lipid phase of emulsomes to increase the zeta potential of the composition, thus stabilizing the particles.

Additionally, the incorporation of these negatively charged lipid compounds in emulsomes results in the formation of phospholipid bilayers with opposing charges, thus increasing the loading of water-soluble molecules in the aqueous compartments formed by the phospholipid bilayers surrounding the lipid core. This effect results from the larger aqueous spaces between the bilayers caused by the electrostatic repulsion between them. Another beneficial role of the inclusion of negatively charged lipid molecules in emulsomes is to reduce the likelihood of particle aggregation, which minimizes destabilizing processes such as coalescence, flocculation, or fusion. Aggregation is prevented by the repulsive forces between the approaching particles.

Negatively charged phospholipids such as phosphatidylglycerol have been incorporated into liposomal formulations used in human clinical studies; see, e.g., S. Amselem et al., *J. Pharm. Sci.* (1990) 79, 1045–1052; S. Amselem et al., *J. Liposome Res.* (1992) 2, 93–123. The significance of zeta potential in analyzing and predicting the properties of phospholipid bilayers is discussed in L. Sai-lung, Chapter 19, Vol. 1 in *"Liposome Technology,"* 2nd ed., G. Gregoriadis, ed., CRC Press, Boca Raton, Fla. (1993), pp. 331–342. Both lipoidal particle size and particle stability vary as a function of zeta potential. For liposomes, zeta potential and particle size increase in proportion to the content of negatively charged phospholipid, up to 50 weight % of negatively charged phospholipid.

The preferred range of negatively charged lipid in emulsome particles is 0 to 30 mol % relative to total phospholipid and charged lipid, more preferably 5 to 20 mol %, and still more preferably 7 to 15 mol %.

Incorporation of Immunogens

Emulsomes for use as vaccine vehicles contain an antigen of interest, usually an antigen bearing at least one epitope which is present on an organism which is a pathogen in the animal species to be vaccinated. In most cases, the antigen is a peptide, a protein, or a glycoprotein. However, other antigenic structures may be employed, including polysaccharides, glycolipids, or a hapten conjugated to a carrier.

Since the emulsome particles provide a soluble or lipid-soluble immunogens can be incorporated in emulsome vaccines of the present invention. Examples of peptide antigens are: hydrophilic natural or synthetic peptides and proteins derived from bacteria, viruses and parasites, such as the recombinant gp160 envelope protein of the HIV virus; natural or synthetic glycoproteins derived from parasites, bacteria or viruses such as the native surface glycoprotein of Leishmania strain or subunit vaccines containing part of the glycopeptides alone or covalently conjugated to lipopeptides like lauryl-cystein hydrophobic foot; protein toxoids such as the Staphylococcus enterotoxin B toxoid, either chemically or physically inactivated; non-toxic bacterial surface structures (fimbrial adhesions) of *Escherichia coli* strains such as the Shiga-like Toxin B Subunit (SLT-B) and AF-R1, a pilus adhesion which is a virulence factor for RDEC-1 *E. coli* strain; outer membrane proteins of *Neisseria meningitidis*; Hepatitis B surface antigen; native or synthetic malaria antigens derived from different portions of *Plasmodium falciparum*, etc. Examples of lipophilic or hydrophobic immunogens are lipopolysaccharides (LPS), such as detoxified LPS obtained from *E. coli* (Sigma Chemical Co., St. Louis, U.S.A.); Lipid A, the terminal portion of LPS, such as the one isolated from *Salmonella minnesota* R595 from List Biological Laboratories (California, U.S.A.).

In some embodiments, the emulsome particles will be free or substantially free of the above or other nonbioactive proteins, i.e. less than 5%, usually less than 1%, and frequently less than 0.1% (w/w) protein relative to other particle components.

In making a vaccine with emulsome vehicle, the antigen of interest may be added to the organic solution of core lipid and phospholipid prior to forming a lipid film. The antigen is thereby integrally associated into the structure of the lipid particles as they are formed. Alternatively, the antigen of interest may be present in the aqueous suspension of lipid particles prior to homogenization, or even added after homogenization. The latter method of preparation tends to produce more superficial binding of the antigen to the lipid particles.

Continuous Aqueous Phase

The aqueous component will be the continuous phase of the emulsome formulation and may be water, saline or any other suitable aqueous solution which can yield an isotonic and pH controlled preparation.

In addition, the compositions of the invention may also comprise conventional additives such as preservatives, osmotic agents or pressure regulators and antioxidants. Typical preservatives include Thimerosal, chlorbutanol, benzalkonium chloride, and methyl, ethyl, propyl or butyl parabens. Typical osmotic pressure regulators include glycerol and mannitol, with glycerol being preferred. The preferred oil phase antioxidant is tocopherol or tocopherol succinate. The aqueous phase may also include an antioxidant of a polyamine carboxylic acid such as ethylene pharino tetra-acetic acid, or a pharmaceutically acceptable salt thereof.

Mucoadhesive Emulsome Vaccines

Emulsome vaccine of the present invention optionally may contain a bioadhesive macromolecule or polymer in an amount sufficient to confer bioadhesive properties. The bioadhesive macromolecule enhances the delivery and attachment of antigens on or through the target mucous surface conferring mucosal immunity. The bioadhesive macromolecule may be selected from acidic non-naturally occurring polymers, preferably having at least one acidic group per four repeating or monomeric subunit moieties, such as polyacrylic acid and/or polymethacrylic acid (e.g. Carbopol, Carbomer), poly(methylvinyl ether/maleic anhydride) copolymer, and their mixtures and copolymers; acidic synthetically modified natural polymers, such as carboxymethylcellulose (CMC); neutral synthetically modified natural polymers, such as (hydroxypropyl) methylcellulose; basic amine-bearing polymers such as chitosan; acidic polymers obtainable from natural sources, such as alginic acid, hyaluronic acid, pectin, gum tragacanth, and karaya gum; and neutral non-naturally occurring polymers, such as polyvinylalcohol; or their mixtures.

The ionizable polymers may be present as free acids, bases, or salts, usually in a final concentration of 0.01–0.5% (w/v).

As used herein, a polymer of an indicated monomeric subunit contains at least 75%, preferably at least 90%, and up to 100% of the indicated type of monomer subunit; a copolymer of an indicated type of monomeric subunit contains at least 10%, preferably at least 25% of that monomeric subunit.

A preferred bioadhesive macromolecule is the family of acrylic acid polymers and copolymers (e.g. CARBOPOL™). These contain the general structure:

$$-[-CH_2-CH(COOH)-]-n$$

One preferred group of polymers of acrylic acid is commercially available under the tradename Carbopol. Carbopol 934 is available in a pharmaceutical grade.

Preferred bioadhesive or mucoadhesive macromolecules have a molecular weight of at least 50 kDa, preferably at least 300 kDA, and most preferably at least 1,000 kDa. Favored polymeric ionizable mucoadhesive macromolecules have not less than 2 mole percent acidic groups (e.g. COOH, $SO_3H$) or basic groups ($NH_2$, NRH, $NR_2$), relative to the number of monomeric units. More preferably, the acidic or basic groups constitute at least 5 mole percent, more preferably 25 or even 50, up to 100 mole % relative to the number of monomeric units of the macromolecule.

Preferred macromolecules also are soluble in water throughout their relevant concentration range (0.01–0.5% w/v).

Polymeric Coating of Emulsomes

Biodegradable polymers may be incorporated to surround or form part of the hydrophobic core of emulsomes. Polymeric emulsomes may contain biodegradable nonnatural polymers such as polyesters of lactic and glycolic acids, polyanhydrides, polycaprolactones, polyphosphazenes and polyorthoesters, or natural polymers such as gelatin, albumin, and collagen. The advantage of polymeric emulsomes is to provide controlled release for the parenteral delivery of drugs and biological compounds in a sustained dosage form.

The structure, selection, and use of degradable polymers in drug delivery vehicles have been reviewed in a recent publication (A. Domb, S. Amselem, J. Shah and M. Maniar, *Polymers for Advanced Technologies* (1992) 3, 279–292). Further guidance to selection of polymers is available in any standard text on that topic.

In general, the ratio of polymer to lipid core (e.g., triglyceride) may be up to 50% (w/w). For the natural protein polymers such as gelatin, which swell extensively in aqueous solution, useful levels of encapsulation may be achieved with much lower amounts of polymer, such as 1% to 10% (w/w).

For most non-natural polymers, which are soluble in organic solvents, the polymer may be codissolved with the triglyceride and phospholipid prior to the evaporation step. For natural polymers which are soluble in aqueous solution, the polymer may be dissolved in the solution used.

Dehydrated Emulsomes

A further aspect of the invention provides dehydrated emulsomes, made by dehydrating the compositions of the types described herein. Dehydration may be performed by standard methods, such as drying under reduced pressure;

when the emulsion is frozen prior to dehydration, this low pressure evaporation is known as lyophilization. Freezing may be performed conveniently in a dry ice-acetone or ethyl alcohol bath. The pressure reduction may be achieved conveniently with a mechanical vacuum pump, usually fitted with a liquid nitrogen cold trap to protect the pump from contamination. Pressures in the low millitorr range, e.g. 10–50 millitorr, are routinely achievable but higher or lower pressures are sufficient.

Emulsomes can be lyophilized by adding cryoprotectants such as sugars or amino acids, and stored as freeze-dried solid material that can be reconstituted with the aqueous medium before us, thus conferring further stability of the incorporated antigens.

Preferred cryoprotectants include sugars such as glucose, sucrose, lactose, maltose, and trehalose; polysaccharides such as dextrose, dextrins, and cyclodextrins; nonnatural polymers such as polyvinylpyrrolidone (PVP); and amino acids. The preferred range of cryoprotectant to emulsome phospholipid is 0.1% up to 10% (w/w).

Dehydration of an emulsome nanoemulsion yields a solid residue which may be stored for prolonged periods, and may be rehydrated to yield an emulsome nanoemulsion having an average particle size similar to that of the original nanoemulsion. The dehydrated emulsomes also retain substantial amounts of the originally incorporated antigen.

The amount of water remaining in the dehydrated emulsome preparation may vary widely depending upon the type and extent of dehydration procedure employed. In general, the dehydrated emulsomes contain less than 1% water by weight, especially when dehydrated by lyophilization. However, stable dehydrated preparations may contain up to 5% water.

Dry compositions for preparing submicron emulsions are disclosed in detail in PCT International Application No. PCT/US93/01415, which was filed on 17 Feb. 1993, and published as WO 93/15736 on 19 Aug. 1993. The disclosure of said document is expressly incorporated herein in its entirety by this reference thereto.

Distinctive Features of Emulsomes

Emulsomes of this invention are distinct from standard oil-in-water emulsions. Due to the high phospholipid content of the current invention, a monolayer of phospholipid surrounds the lipid core at the aqueous interface thereby stabilizing the emulsion. In addition, one or more bilayers or envelopes of phospholipid molecules are believed to form around the particles in many embodiments. Another major difference is that while standard oil-in-water emulsions are dispersions of one liquid into another, emulsomes are dispersions of a solid in a liquid.

The main differences between oil-in-water emulsions and emulsomes are summarized in Table 1.

One major drawback of standard oil-in-water emulsions is limited drug loading. When drug encapsulation above 1% is required, a correspondingly larger oil phase (10–20%) is required to dissolve the drug. However, the high oil content reduces the stability of the emulsion, and the addition of a surfactant or cosurfactants, is necessary. Due to the detergent properties of most surfactant compounds, their use for parenteral administration is very limited. Many toxic reactions have been reported even with the surfactants already approved for parenteral formulations, such as sodium deoxycholate, poloxamer-188 (Pluronic F-68), polysorbate 80 (TWEEN 80), and Emulphor EL-620 or polyethoxylated castor oil.

The pharmaceutically stable emulsomes described herein have major advantages over standard emulsions in that water-soluble and water insoluble antigens can be encapsulated either separately or simultaneously at high loadings in the absence of any nonnatural ionic or non-ionic surfactant.

TABLE 1

| Definition | SME Dispersion of an oil in water | Emulsome Dispersion of a solid fat or lipid in water | Liposome Dispersion of phospholipids in water |
|---|---|---|---|
| Internal core | oil | solid or liquid crystalline lipid | water |
| Phospholipid content (w/v) | 0.5–2% | 5–10% | 0.1–5% |
| Non-natural surfactant | present | usually absent | usually absent |
| Co-surfactant | present | usually absent | usually absent |
| Lipophilic loading | up to 10 mg/ml | up to 100 mg/ml | up to 20 mg/ml |
| PC/total lipid (mol/mol) | 0.01–0.1 | 0.1–0.5 | 0.6–1.0 |

Emulsomes of this invention differ from the microdroplets of U.S. Pat. Nos. 4,725,442 and 4,622,219. Microdroplets, originally called monolayer vesicles, consist of spheres of organic liquid covered by one monolayer of phospholipid, while the internal core of emulsomes consists of a solid lipid or fat. The phospholipid content of microdroplets is low (about 1.2%) forming only one monolayer, while in emulsomes the phospholipid content is high (5–10%) and in certain embodiments is believed to form several bilayers surrounding the fat core. Another major difference between microdroplets and emulsomes is that microdroplets are useful only for water-insoluble compounds, while in emulsomes, due to the high lecithin content, water-soluble as well as water-insoluble compounds can be incorporated.

Methods of Preparation of Emulsomes

A further embodiment of the invention relates to methods for preparation of emulsome vaccines intrinsically and extrinsically as extensively detailed in the examples. In general, emulsome intrinsic formulations are prepared by emulsifying the antigen together with the emulsome components, while emulsome extrinsic formulations are prepared by adding externally the antigen to previously prepared plain emulsomes.

Emulsomes may be prepared by mixing phospholipids and triglycerides in a weight ratio range of 0.5:1 wherein the triglyceride has a solid to liquid phase transition temperature of greater than 25° C.; suspending the mixture in an aqueous solution at a temperature below the solid to liquid transition temperature of the triglyceride; and homogenizing or otherwise reducing the suspension to yield the emulsomes. These emulsomes comprise a nanoemulsion of lipid particles having a mean particle diameter of between about 10 nm and 250 nm, usually within the range 20 to 180 nm, and frequently within the range 50 to 150 nm.

These size ranges preferably are determined on a weight percent basis, rather than a particle number basis. The cited ranges include the mean particle size. In certain embodiments, the cited ranges include the mean plus or minus the standard error, and in other embodiments the cited ranges include at least 99% of the particles as determined on a weight basis.

Conveniently, the lipid components may be dissolved in a volatile and chemically unreactive organic solvent such as dichloromethane or diethyl ether. The organic solvent is removed, typically under reduced pressure in a rotary evaporator or under a stream of inert gas. The resulting lipid film is hydrated and dispersed by covering and shaking with an aqueous solution. The immunogen to be incorporated according to its chemical properties and hydrophilic-lipophilic nature can be included in the lipid phase or may be added to the aqueous hydration solution.

Water-soluble antigens are encapsulated or entrapped in emulsomes by dissolving them in the aqueous medium, hydrating the dry fat-phospholipid mixture with the aqueous phase containing the antigen utilizing mechanical shaking, and sizing the resultant dispersion by high shear-homogenization to the desired final size range.

Lipid-soluble antigens may be incorporated into solid lipid nanoemulsions by dissolving them in a suitable organic solvent together with the lipid ingredients of the composition, e.g., phospholipids and solid fatty acid esters, evaporating the solvent to complete dryness, hydrating the antigen-lipid mixture with the aqueous phase utilizing mechanical shaking, and homogenizing the resultant dispersion with high-shear homogenizers to final sizes in the range of 10 to 250 nm.

The lipid suspension or dispersion is then sized, typically by high shear homogenization at pressures up to 800 bar in a Gaulin-type homogenizer (AVP Gaulin International, Holland) or EmulsiFlex™ homogenizer (Avestin Inc., Canada). High pressure Gaulin homogenization is described in detail in Brandl et al., in *Liposome Technology*, 2nd ed., G. Gregoriadis, ed., Vol. 1, Ch. 3, CRC Press, Boca Raton, Fla., (1993), pp. 49–65.

Emulsomes also may be prepared by high pressure extrusion through polycarbonate membranes. In this procedure, the sizing step on the lipid dispersion is performed using a pressure extruder, such as the stainless steel GH76-400 Extruder or Pressure Cell (Nucleopore, U.S.A.), rather than a high-shear homogenizer. The pressure extruder and the extrusion technique for liposome preparation are described in detail in S. Amselem et al., in *Liposome Technology*, 2nd ed., G. Gregoriadis, ed., Vol. 1, Ch. 28, CRC Press, Boca Raton, Fla., (1993), pp 501–525.

Due to the small size of emulsomes they can be sterilized by final sterile filtration through 0.2 μm filter membranes.

EXAMPLES

This invention is illustrated by the following non-limiting examples:

Example 1

PREPARATION OF EMULSOMES USING A HIGH SHEAR MICROLAB 70 GAULIN HOMOGENIZER

To a 0.5 liter round-bottomed flask, 2.5 g of egg-lecithin, 2.5 g of tricaprin, 0.1 g of cholesterol, 0.1 g of oleic acid and 0.01 g of tocopherol succinate were added. The lipid mixture was dissolved in 50 ml dichloromethane. The organic solvent was evaporated until complete dryness under reduced pressure using a rotary evaporator (Heidolph, Germany). To the dry lipid film 50 ml of saline were added and the mixture was then hydrated by shaking until all the lipids were homogeneously dispersed in the aqueous phase. The dispersion was homogenized for five minutes at 15,000 rpm using a Polytron PT 3000 (Kinematica, AG). The preparation was then submitted to 10–15 cycles of high shear homogenization at 800 bar using a Microlab 70 Gaulin Homogenizer (AVP Gaulin International, Holland). The particle size distribution of the formulation was determined using a N4MD Coulter Particle Size Analyzer (Coulter Electronics, England). The differential weight % mode of the instrument indicated the existence of a single homogeneous population of emulsomes with a mean particle diameter of 84±32 nm. The formulation was shown to be stable at room temperature for several months without changes in the mean size of the particles.

Example 2

PREPARATION OF EMULSOMES USING A EMULSIFLEX™ HOMOGENIZER

Figure 2:
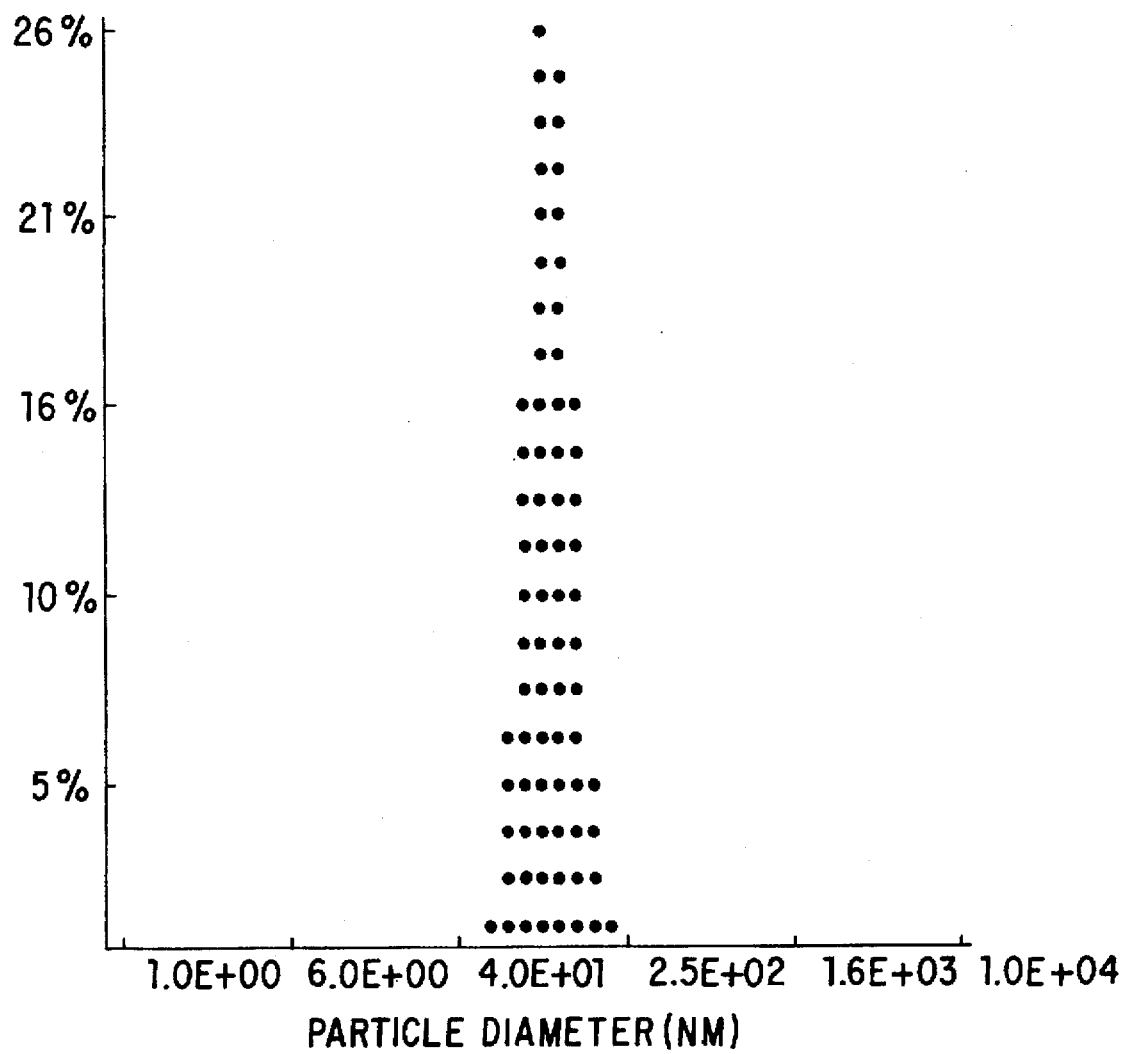
FIG. 2 is a graph showing the particle size distribution, as differential weight percent, of a group of emulsomes according to the present invention.

To a 0.5 liter round-bottomed flask, 3.5 g of egg-lecithin, 3.5 g of tricaprin, 0.2 g of cholesterol, 0.2 g of oleic acid, and 0.05 g of tocopherol succinate were added. The lipid mixture was dissolved in 50 ml dichloromethane. The organic solvent was evaporated until complete dryness under reduced pressure using a rotary evaporator (Heidolph, Germany). To the dry lipid film 70 ml of saline were added and the mixture was then hydrated by shaking until all the lipids were homogeneously dispersed in the aqueous phase (estimated hydration time, 1 hr). The dispersion was homogenized by submitting the preparation to 5–7 cycles of high shear homogenization at 12,500 psi working pressure using a EmulsiFlex™ C30 Homogenizer (Avestin Inc., Canada). The particle size distribution of the resultant emulsomes was determined using a N4MD Coulter Particle Size Analyzer (Coulter Electronics, England). The differential weight % mode of the instrument indicated the existence of a single homogeneous population of emulsomes with a mean particle diameter of 109±30 nm. FIG. 2 shows the particle size distribution of emulsomes prepared by EmulsiFlex™ instrument.

Example 3

CHARACTERIZATION OF EMULSOME PARTICLES

The parameters most frequently used to characterize lipid particles are particle size and size distribution, morphology, and lamellarity. Emulsome structure was demonstrated and characterized by several techniques including electron microscopy, photon correlation spectroscopy, and NMR.

Particle Size Distribution:

The particle size distribution of the emulsome formulations were determined by photon correlation spectroscopy (PCS), based on measuring laser scattered-light fluctuations, using a N4MD Coulter Submicron Particle Size Analyzer (Coulter Electronics, England) working at the differential weight % operation mode of the instrument (Barenholz, Y., and Amselem, S. In *"Liposome Technology"*, Gregoriadis G., ed., 2nd edition, Vol. 1, pp 527–616, CRC press, Florida, 1993).

The particle size distribution of all emulsome formulations described in the Examples was determined by photon correlation spectroscopy using the N4MD Coulter. The N4MD Coulter submicron particle analyzer, indicated the existence of a single homogeneous population of Emulsomes with a mean particle diameter in the range of 50–200 nm (FIG. 2).

Figure 3A:
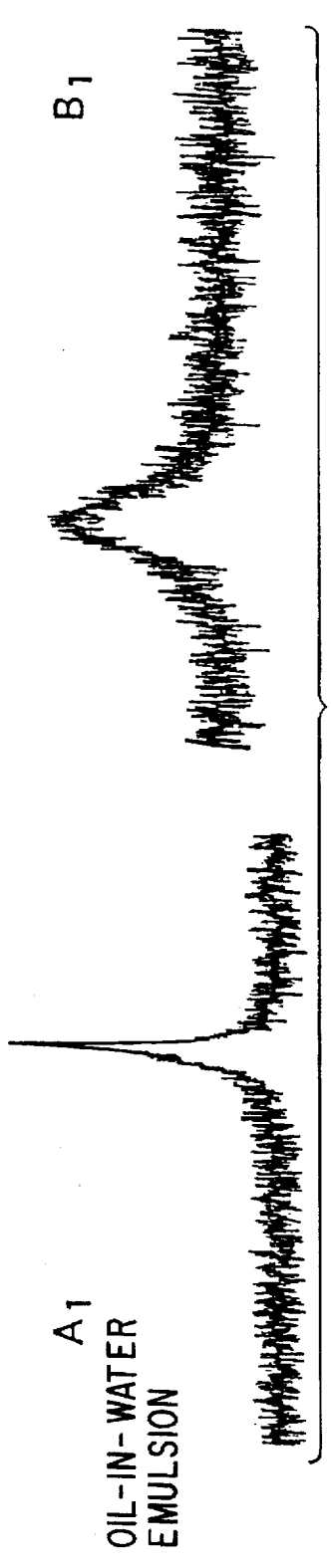
FIGS. 3A–C compares the $^{31}$P-NMR spectra of submicron oil-in-water emulsion, emulsomes, and liposomes, recorded in the absence ("A" series) and presence ("B" series) of PrCl$_3$ (30 mM).

$^{31}$P-NMR measurements:

One of the most accurate and straightforward procedures for quantitatively determining the lamellarity of phospholipid dispersions is to use NMR spectroscopy and especially $^{31}$P-NMR signal to monitor the phospholipid phosphorous signal intensity (Lichtenberg, D., Amselem, S., and Tamir, I. *Biochemistry*, 18, 4169–4172, 1979). In particular, adding an impermeable paramagnetic shift reagent to the external medium will decrease the intensity of the initial $^{31}$P-NMR signal by an amount proportional to the fraction of lipid exposed to the external medium. FIG. 3 shows phosphorous nuclear magnetic resonance ($^{31}$P-NMR) spectra of liposomes, emulsomes, and submicron oil-in-water emulsion recorded before and after the addition of the lanthanide ion $Pr^{+3}$. The $^{31}$P-NMR spectra were recorded on a Brucker AM400 instrument employing a 50 KHz sweep width, 3 sec interpulse delay and broadening proton decoupling. Phosphoric acid in $D_2O$ was used as standard for 0 ppm chemical shift.

Figure 1B:
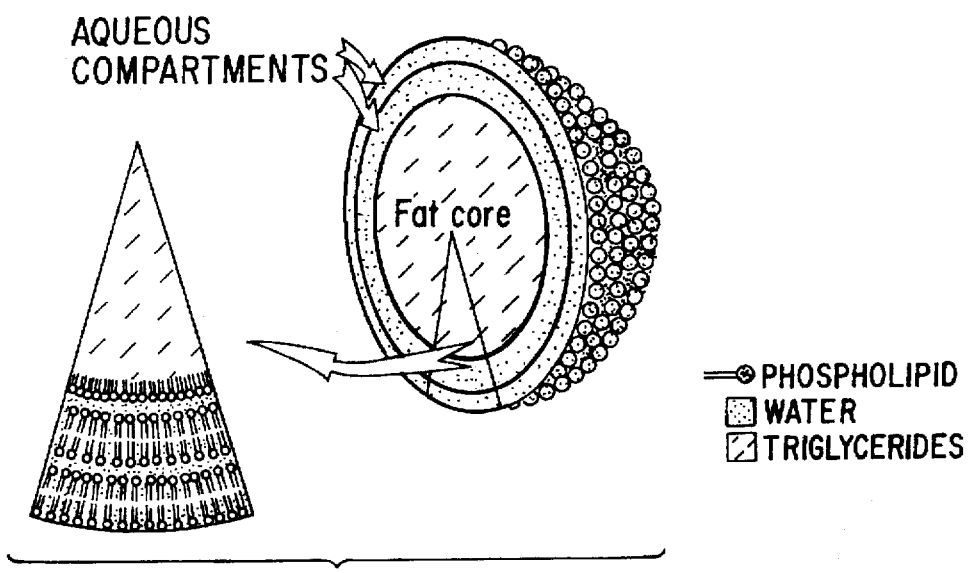
Figure 1C:
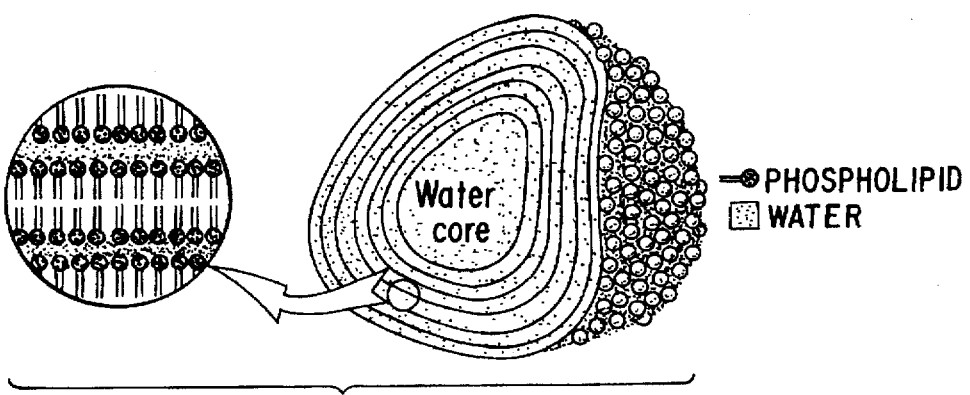
Figure 3B:
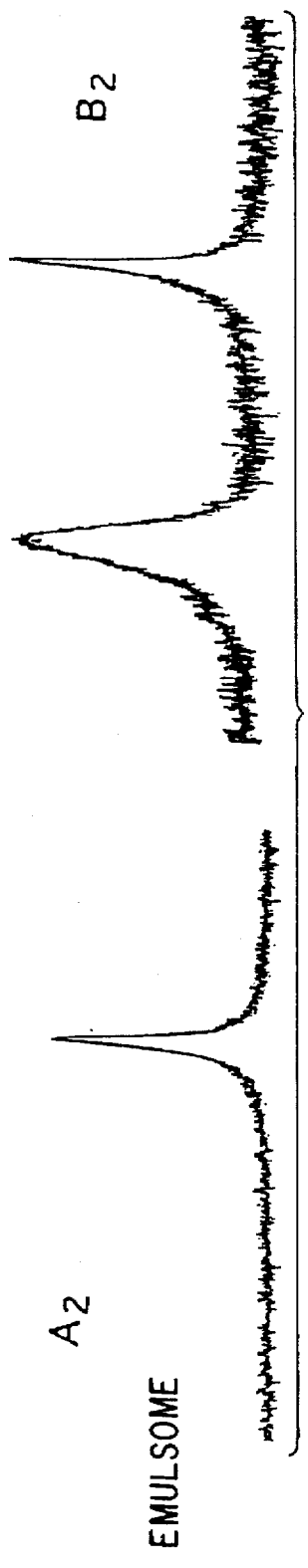
Figure 3C:
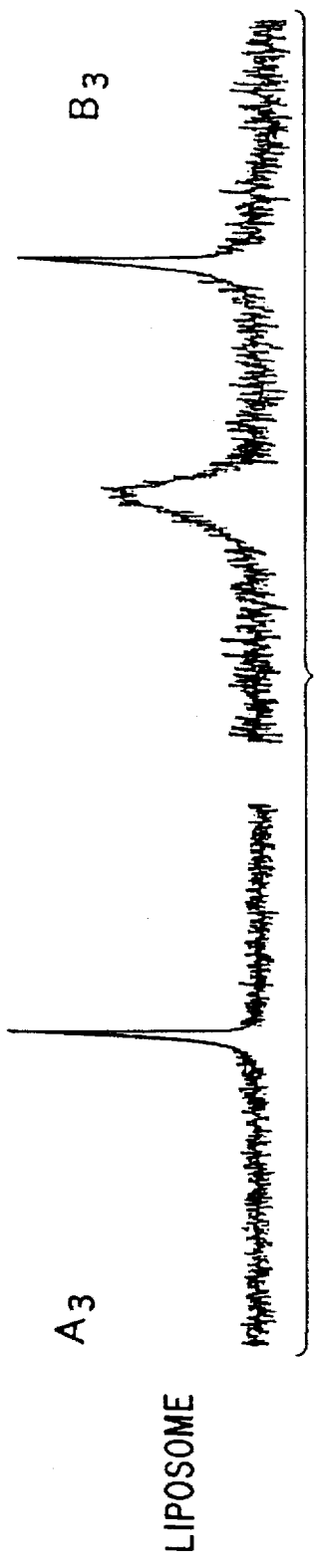

For the submicron oil-in-water emulsion (SME) after the addition of the paramagnetic ion the whole $^{31}$P-NMR signal was shifted downfield (FIG. 3B1). This result is expected since in the SME all the phospholipid molecules are located in the surface of the emulsion oil droplets as a monolayer, thus the $Pr^{+3}$ ions interact with all the exposed phospholipid molecules. On the other hand for emulsomes, the $^{31}$P-NMR signal was split into two peaks after Pr+3 addition (FIG. 3B2), indicating that only a portion of the phospholipid molecules (those in the outer monolayer exposed to the aqueous medium) interacted with the $Pr^{+3}$ ions demonstrating the existence of bilayer structures. The same picture was obtained for small unilamellar liposomes (FIG. 3B3) used as control, where the existence of phospholipid bilayer domains have been well documented (Barenholz, Y., and Amselem, S. In *"Liposome Technology"*, Gregoriadis G., ed., 2nd edition, Vol. 1, pp. 527–616, CRC press, Florida, 1993).

Figure 4:
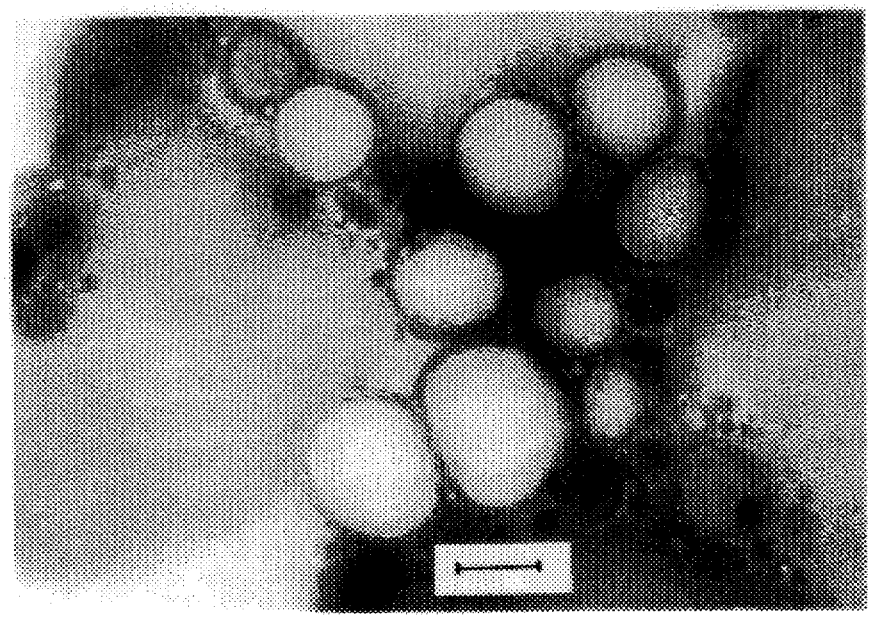
FIG. 4 is a transmission electron micrograph of emulsome preparation negatively stained with 1% phosphotungstic acid solution (Bar=100 nm).

Electron microscopy:

Negative stain electron microscopy (EM) has been used to characterize the size and shape of the lipid particles present in phospholipid dispersions. EM gives also a gross estimate of lamellarity since stain penetrates interbilayer spaces and allows lamellae to be resolved. FIG. 4 is an transmission electron micrograph of emulsome preparation showing spheric particles having a diameter in the range of 80–130 nm surrounded by well-defined phospholipid bilayers enveloping the internal hydrophobic core made of triglycerides.

Example 4

PREPARATION OF EXTRINSIC MUCOADHESIVE EMULSOME VACCINE

To a round 0.5 liter round-bottomed flask, 1.75 gr of egg-lecithin, 1.75 gr of tricaprin, 70 mg of cholesterol, 70 mg of oleic acid, and 7 mg of tocopherol succinate were added. The lipid mixture was dissolved in 50 ml of chloroform. The organic solvent was evaporated until complete dryness under reduced pressure using a rotary evaporator (Heidolph, Germany). To the dry lipid film 60 ml of aqueous solution containing 0.1% EDTA were added and the mixture was then hydrated by shaking or 30 min. using a multiwrist shaker (Labline, U.S.A.) until all the lipids were homogeneously dispersed in the aqueous phase. The dispersion was homogenized using a Microlab 70 Gaulin Homogenizer (5 cycles at 800 bar). The particle size distribution of the resultant emulsomes was determined using a N4MD Coulter Particle Size Analyzer (Coulter Electronics, England). The indicated the existence of a single homogeneous population of emulsomes with a mean particle diameter of 140±50 nm. Then 6.72 gr of a 1% Carbopol solution was added and stirred for 20 min to confer mucoadhesive properties to the emulsome preparation. Glycerol (1.44 gr) were added thereafter to reach a physiological osmolarity (269 mOsm). The pH was adjusted to 6.0 using a 1M NaOH solution. To this plain mucoadhesive emulsome preparation, antigens can be added extrinsically and mixed with the emulsome carrier particles by gentle shaking in order to obtain the proper emulsome vaccine.

Example 5

PREPARATION OF INTRINSIC HEPATITIS B EMULSOME VACCINE

To a round 0.25 liter round-bottomed flask, 2.5 gr of egg-lecithin, 2.5 gr of tricaprin, 100 mg of cholesterol, 100 mg of oleic acid, and 10 mg of tocopherol succinate were added. The lipid mixture was dissolved in 25 ml of chloroform. The organic solvent was evaporated until complete dryness under reduced pressure using a rotary evaporator (Heidolph, Germany). To the dry lipid film 60 ml of phosphate buffered saline containing 0.5 mg of Hepatitis B antigen were added and the mixture was then hydrated by shaking for 30 min using a Multiwrist shaker (Labline, U.S.A.) until all the lipids were homogeneously dispersed in the aqueous phase. The dispersion was homogenized using a Microlab 70 Gaulin Homogenizer (5 cycles at 800 bar). The particle size distribution of the resultant emulsomes was determined using a N4MD Coulter Particle Size Analyzer (Coulter Electronics, England). The differential weight % mode of the instrument indicated the existence of a single homogeneous population of emulsomes with a mean particle diameter of 105+24 nm. The emulsome vaccine formulation was then 2-fold concentrated using a Filtron ultrafiltration stirred cell (Omega Series membrane with 10,000 molecular weight cutoff, Filtron Technology Corp., Massachusettes).

Example 6

PREPARATION OF MUCOADHESIVE INTRINSIC ANTI-HIV ENVELOPE PROTEIN (gp160) EMULSOME VACCINE

Antigen description and background: The urgency and high priority for developing an effective vaccine against the human immunodeficiency virus (HIV) are fully recognized. The reasons for using subunits of the virus as the basis of an HIV vaccine are the perceived overwhelming requirements for safety. Despite the high efficacy of many live attenuated viral vaccines, the requirement for product safety, especially in the case of retroviruses, has favored the subunit approach to the extent that all of the current candidate preparations in clinical prophylactic trials are of this type, being mainly gp160, the envelope protein of HIV, or part thereof. Studies have shown that gp160 attaches the virus to the cell and also facilitates the fusion of the cell and virus during the early stages of infection.

Emulsome preparation:

To a round 0.25 liter round-bottomed flask, 0.24 gr of egg-lecithin, 0.24 gr of tricaprin, 20 mg of cholesterol, and 20 mg of oleic acid, and 2 mg of tocopherol succinate were added. The lipid mixture was dissolved in 50 ml of chloroform. The organic solvent was evaporated until complete dryness under reduced pressure using a rotary evaporator (Heidolph, Germany). To the dry lipid film 60 ml of aqueous solution containing 0.18 mg of gp160 antigen and 0.1% EDTA were added and the mixture was then hydrated by shaking for 30 min. using a multiwrist shaker (Labline, U.S.A.) until all the lipids were homogeneously dispersed in the aqueous phase. The dispersion was homogenized using a Microlab 70 Gaulin Homogenizer (6 cycles at 800 bar). The particle size distribution of the resultant emulsomes was determined using a N4MD Coulter Particle Size Analyzer (Coulter Electronics, England). The differential weight % mode of the instrument indicated the existence of a single homogeneous population of emulsomes with a mean particle diameter of 158±57 nm. The emulsome vaccine formulation was then 5-fold concentrated using a Filtron ultrafiltration stirred cell (Omega Series membrane with 10,000 molecular weight cutoff, Filtron Technology Corp., Massachusetts). Then 1.3 gr of a 1% Carbopol solution was added and stirred for 15 min to confer mucoadhesive properties to the emulsome vaccine preparation. Glycerol (0.285 gr) were added thereafter to reach a physiological osmolarity. The pH was adjusted to 6.0 using a 0.5M NaOH solution. The estimated final gp160 concentration in the formulation was 15 µg/ml.

Example 7

PREPARATION OF MUCOADHESIVE INTRINSIC EMULSOME VACCINE CONTAINING ANTI-HIV ENVELOPE PROTEIN (gp160) COMPLEXED TO PROTEOSOMES

Proteosomes are meningococcal outer membrane protein preparations purified from *Neisseria meningitidis* by detergent extraction and ammonium sulphate precipitation. They naturally form 20–100 nm diameter hydrophobic membranous vesicles. Antigens are non-covalently complexed to proteosomes via hydrophobic interactions by mixing the antigen and proteosomes in the presence of detergent and then removing the detergent over a prescribed period of time, permitting hydrophobic interactions to occur in the system.

Proteosomes have previously been shown to enhance the parenteral immunogenicity of peptides, gangliosides, lipopolysaccharides and proteins hydrophobically complexed to them (Lowell, G. H., L. F. Smith, R. C. Seid and W. D. Zollinger, *J. Exp. Med.* 167, 658–663, 1988). (Lowell, G. H., W. R. Ballou, L. F. Smith, R. A. Wirtz, W. D. Zollinger and W. T. Hockmeyer. *Science* 240, 800–802, 1988; Lowell, G. H. 1990. In: *"New Generation Vaccines"*. G. C. Woodrow and M. M. Levine (eds.), Marcel Dekker, Inc., New York, p. 141–160) and have been shown to be safe for human use in vaccine trials involving tens of thousands of humans in the development of anti-meningococcal vaccines (Zollinger, W. D. New and Improved Vaccines Against Meningococcal Disease. In: *"New Generation Vaccines"*, G. C. Woodrow and M. M. Levine (eds.), Marcel Dekker, Inc., New York, p. 325–348). Furthermore, proteosomes confer mucosal immunogenicity upon non-immunogenic antigens when administered orally or intranasally. Such intranasal or oral proteosome vaccines induce up to 100% protection against lethal pneumonia or keratoconjunctivitis in experimental murine models of shigellosis (Orr, N., G. Robin, D. Cohen, R. Arnon and G. Lowell. 1993. Immunogenicity and efficacy of oral or intranasal *Shigella flexneri* 2a and *Shigella sonnei* proteosome-lipopolysaccharide vaccines in animal models. *Infect. Immun.* 61, 2390–2395).

Lipid and aqueous phases were prepared as described in Example 6. A vial containing 0.18 mg of gp160 non-covalently complexed to proteosomes and suspended in saline was added to the water phase (60 ml total volume) and the mixture was gently shaken for 5 min. The subsequent steps involved in the preparation of the mucoadhesive emulsome vaccine were carried out as described in Example 6. The particle size volume % distribution of the resultant emulsome formulation showed a mean droplet size of 112 nm. The estimated final gp160 concentration in the formulation was 15 µg/ml.

Example 8

PREPARATION OF MUCOADHESIVE EXTRINSIC EMULSOME VACCINE CONTAINING gp160 ALONE OR COMPLEXED TO PROTEOSOMES

Mucoadhesive extrinsic emulsome formulation containing gp160 alone or gp160 complexed non-covalently to proteosomes was performed by preparing plain emulsomes as described in Example 7, but in the absence of the antigen and adding externally an aqueous dispersion of the gp160 or gp160-conjugated to proteosomes to the plain emulsomes by gently shaking for 15 min at room temperature.

Example 9

PREPARATION OF INTRINSIC EMULSOME VACCINE CONTAINING STAPHYLOCOCCUS ENTEROTOXIN B TOXOID-F ANTIGEN

Antigen description and background: Staphylococcal enterotoxin B (SEB) is a potent toxin that causes food borne illness among civilians and military personnel stationed around the world and is identified as a lethal offensive military threat that endangers both military and civilian populations through aerosolization.

SEB infection in civilian populations is related to staphylococcal food poisoning by SEB and related toxins: also contributes to death from staphylococcal sepsis following overwhelming staph infection. It also causes staph scalded skin syndrome in kids—i.e. morbidity and mortality from staphylococcal infections (P. Marrack and J. Kappler, *Science*, 248,705–711, 1990).

Due to the similarity to the human response both in sensitivity and clinical signs and the lack of an established model for lethality to SEB delivered via the respiratory route in lower animal species, non-human primates have been the primary animal model for development of vaccines to protect against respiratory challenge with SEB. Early work indicated that monkeys develop decreased sensitivity to repeated mucosal administration of the toxin. This suggested that protection to SEB exposure might be provided by toxoid immunization. Studies in rhesus monkeys and other animals indicated that oral immunization with formalinized toxoid was ineffective against parenteral challenge whereas parenteral immunization with formalinized SEB toxid induced serum antibodies that recognized native SEB (Bergdoll, M. S. Enterotoxins. pp. 559–598 In: *Staphylococci and Staphylococcal Infections*, eds. C. S. F. Easmon and C. Adlam, Academic Press, London, 1983). In the latter studies, however, several parenterally immunized monkeys that acquired anti-SEB antibodies had severe immediate-type hypersensitivity reactions when challenged with SEB toxin. These adverse reactions suggested that the formalinized SEB toxoid alone was not a candidate for parenteral vaccine development. Additionally, as the military threat would be by aerosolization, it was determined that studies on protection provided by serum IgG to respiratory challenge as well as protective effects provided by anti-SEB secretory IgA in the respiratory tract were required.

Recently, two identical lots of formalinized SEB toxoid were made at Walter Reed Army Institute of Research, Washington DC (WRAIR) following previously described specifications (Kaminski, R., S. Grate, E. Aboud-Pirak, C. Hooper, T. Levin, I. Weiss, S. Amselem, R. Arnon and G. Lowell, 1993. In: *Proceedings of* 1993 *Medical Defense Bioscience Review*, Baltimore, Md.). This WRAIR formalinized toxoid preparation designated Tox-F was non-toxic in rabbits at 0.5 mg/kg, the dose at which SEB toxin is invariably lethal. Furthermore, it was non-toxic in the murine D-galactosamine model of SEB toxicity even at 500 µg per BALB/c mouse; 50 µg of SEB is 100% lethal in such mice. The physical characteristics of Tox-F were similar to that described by Eldridge (Eldridge, J. H., Staas, J. K., Meulbroek, J. A., Tice, T. T. and Gilley, R. M. Biodegradable and biocompatible poly(DL-lactide-co-glycolide) microspheres as an adjuvant for staphylococcal enterotoxin B toxoid which enhances the level of toxin-neutralizing antibodies. (*Infect. Immun.* 59, 2978–2986, 1991) in that SDS-PAGE gel of Tox-F showed two distinct bands with estimated MW of 23,000 and 46,000. Biologically, Tox-F also had the characteristics previously reported by Eldridge et al., namely in a Mouse Spleen Lymphocyte Proliferative Assay in which concentrations of SEB toxin of 0.37–10.0 µg/ml were mitogenic, Tox-F was entirely non-mitogenic at all concentrations tested (0.04–100.0 µg/ml).

Preparation of SEB-Toxoid F:

Formalinized SEB-Toxoid (Tox-F) was prepared according to the method of Warren, J. R., Spero, L. and Metzger, J. F. 1983. *J. Immunol.* 111, 885–892 and as per Eldridge, J. H. et al. 1991, *Infect. Immun.* 59, 2978–2986 by formalin treatment for 30 days at 37 C., pH 7.5.

Preparation of Emulsomes:

To a round 0.5 liter round-bottomed flask, 2.25 gr of egg-lecithin, 2.25 gr of tricaprin, 90 mg of cholesterol, 90 mg of oleic acid, and 9 mg of tocopherol succinate were added. The lipid mixture was dissolved in 50 ml of chloroform. The organic solvent was evaporated until complete dryness under reduced pressure using a rotary evaporator (Heidolph, Germany). To the dry lipid film 50 ml of aqueous solution containing 10 mg of Staphylococcus Enterotoxin B toxoid, glycerol 2.25% and 0.1% EDTA were added and the mixture was then hydrated by shaking until all the lipids were homogeneously dispersed in the aqueous phase. The dispersion was homogenized using a Microlab 70 Gaulin Homogenizer (6 cycles at 800 bar). The particle size distribution of the resultant formulation was determined using an N4MD Coulter Particle Size Analyzer (Coulter Electronics, England). The differential weight % mode of the instrument indicated the existence of a single and homogenous population of emulsome particles with a mean particle size distribution of 115±80 nm. The estimated final antigen concentration in the formulation was 220 µg/ml.

Example 10

PREPARATION OF EXTRINSIC EMULSOME VACCINE CONTAINING STAPHYLOCOCCUS ENTEROTOXIN B-TOXOID-F

Extrinsic formulation of SEB-Toxoid-F in emulsomes was performed by preparing plain emulsomes as described in Example 9, but in the absence of the antigen and adding externally the aqueous solution containing the SEB-Toxoid-F to the plain emulsomes by gently shaking for 15 min at room temperature. A total volume of 0.78 ml of stock plain emulsomes were mixed with 0.78 ml solution of SEB-Toxoid-F (1 mg/ml protein) in 0.15M NaCl and 0.01M Tris buffer to give a final SEB-Toxoid-F concentration of 0.5 mg/ml.

Example 11

PREPARATION OF INTRINSIC EMULSOME VACCINE CONTAINING STAPHYLOCOCCUS ENTEROTOXIN B-TOXOID-F COMPLEXED TO PROTEOSOMES

To a round 0.5 liter round-bottomed flask, 2.5 gr of egg-lecithin, 2.5 gr of tricaprin, 100 mg of cholesterol, and 100 mg of oleic acid, and 10 mg of tocopherol succinate were added. The lipid mixture was dissolved in 50 ml of chloroform. The organic solvent was evaporated until complete dryness under reduced pressure using a rotary evaporator (Heidolph, Germany). To the dry lipid film 50 ml of aqueous solution containing 5 mg of Staphylococcus Enterotoxin B toxoid-F complexed to proteosomes, and glycerol (2.25% w/v) were added and the mixture was then hydrated by shaking until all the lipids were homogeneously dispersed in the aqueous phase. The dispersion was homogenized using a Microlab 70 Gaulin Homogenizer (5 cycles at 800 bar). The particle size distribution of the resultant formulation was determined using an N4MD Coulter Particle Size Analyzer (Coulter Electronics, England). The unimodal mode of the instrument indicated the existence of a single and homogenous population of emulsome particles with a mean particle size distribution of 152±53 nm. The estimated final antigen concentration in the formulation was 100 µg/ml.

Example 12

PREPARATION OF EXTRINSIC EMULSOME VACCINE CONTAINING STAPHYLOCOCCUS ENTEROTOXIN B-TOXOID-F COMPLEXED TO PROTEOSOMES

Extrinsic emulsomes formulation of SEB-Toxoid-F-complexed to proteosomes was performed by preparing plain emulsomes as described in Example 9, but in the absence of the antigen and adding externally the aqueous solution containing the SEB-Toxoid-F complexed to proteosomes to the plain emulsomes by gently shaking for 15 min at room temperature. A total volume of 0.78 ml of stock plain emulsomes were mixed with 0.78 ml solution of SEB-Toxoid-F (1 mg/ml protein) in 0.15M NaCl and 0.01M Tris buffer to give a final SEB-Toxoid-F concentration of 0.5 mg/ml.

Example 13

PREPARATION OF INTRINSIC EMULSOME VACCINE CONTAINING LC-467 LEISHMANIA LIPOPEPTIDE ANTIGEN

Antigen description and background:

The gene for a surface protein antigen of Leishmania major gp63, has been cloned and sequenced. This protein, recombinantly expressed in live Salmonella, or given in a sub-unit vaccine as either the purified native gp63 or selected gp63 peptides (Jardim A., Alexander J., Teh S., Ou D, Olafson R. W. 1990. *J. Exp. Med.* 172, 645), has recently been shown to limit the extent of lesion development in murine models of cutaneous leishmaniasis when given with certain adjuvants. These results suggest that a vaccine to protect humans against leishmaniasis composed of defined purified components is a realistic goal. The sub-unit vaccines were effective, however, only when administered with adjuvants containing *Corynebacterium parrum* (CPV) and poloxamer 407. Other adjuvants (Complete Freund's Adjuvant, CFA), or lack of adjuvant exacerbated disease. Major success was achieved with the discovery that subcutaneous immunization with one small gp63 peptide covalently conjugated to lauryl-cysteine protected against severe Leishmania cutaneous lesions with reduction of lesions in three separate experiments.

Preparation of emulsomes:

To a round 0.25 liter round-bottomed flask, 0.4 gr of egg-lecithin, 0.4 gr of tricaprin, 15 mg of cholesterol, and 15 mg of oleic acid, and 1.5 mg of tocopherol succinate were added. The lipid mixture was dissolved in 50 ml of chloroform. The organic solvent was evaporated until complete dryness under reduced pressure using a rotary evaporator (Heidolph, Germany). To the dry lipid film 50 ml of aqueous solution containing 80 μg of LC-467 Leishmania lipopeptide antigen in phosphate buffered saline were added and the mixture was then hydrated by shaking for 30 min. using a multiwrist shaker (Labline, U.S.A.) until all the lipids were homogeneously dispersed in the aqueous phase. The dispersion was homogenized using a Microlab 70 Gaulin Homogenizer (5 cycles at 800 bar). The particle size distribution of the resultant emulsomes was determined using a N4MD Coulter Particle Size Analyzer (Coulter Electronics, England). The differential weight % mode of the instrument indicated the existence of a single homogeneous population of emulsomes with a mean particle diameter of 181±35 nm. The emulsome vaccine formulations were then 6.5-fold concentrated using a Filtron ultrafiltration stirred cell (Omega Series membrane with 10,000 molecular weight cutoff, Filtron Technology Corp., Massachusettes). The estimated final antigen concentration in the formulation was 0.25 mg/ml.

Example 14

IMMUNOGENICITY OF EMULSOME VACCINE CONTAINING LC-467 LEISHMANIA LIPOPEPTIDE ANTIGEN

The objective in the present example was to demonstrate immunogenicity and efficacy of LC-467 Leishmania lipopeptide emulsome vaccine to protect against severe morbidity of cutaneous leishmaniasis in murine models.

The antigen used were lipopeptides obtained from the major glycoprotein of the Leishmania parasite. The peptide denoted 467 was covalently attached to lauryl cystsine to serve as the hydrophobic foot.

The murine model used, CBA mouse, resembles the human cutaneous disease. The immunization protocol included two injections of the animals (8 mice/group) at weeks 0 and 3 with the experimental vaccines (50 μg peptide/mouse). At week 6 the mice were infected with live Leishmania parasites and the lesion size as function of time was measured and compared. The results were expressed as % decrease from control (saline injection). Immunization of the mice with the LC-467 emulsome formulation enhanced the protective effects (reduction of lesion size) obtained with the free antigen (Table 2).

Since there is considerable homology among Leishmania strains, this peptide may have wide application in ameliorating lesions caused by other forms of Leishmania.

TABLE 2

| Vaccine Formulation | % Protection (reduction of lesion size compared to control mice) |
|---|---|
| LC-467 in saline | 73 |
| LC-467 in emulsomes | 94 |

Example 15

ENHANCED MURINE IMMUNOGENICITY OF SEB TOX-F ANTIGEN AFTER PARENTERAL IMMUNIZATION WITH INTRINSIC EMULSOME VACCINE COMPARED TO FREE ANTIGEN OR ALUM-ADJUVANTED VACCINE

Figure 5:
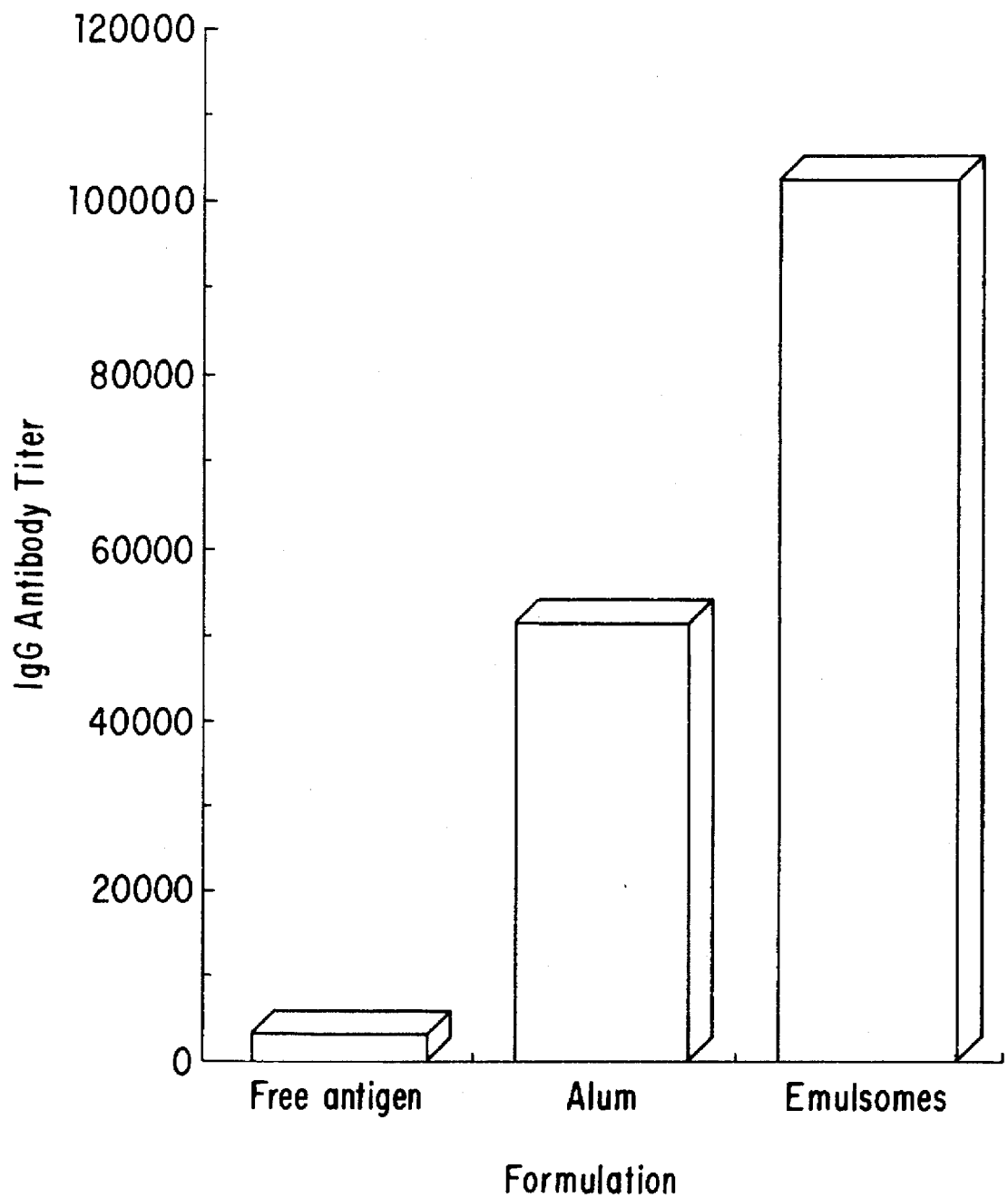
FIG. 5 is a graph showing enhanced murine immunogenicity after parenteral immunization of mice with formalinized SEB-Toxoid antigen formulated in intrinsic emulsome vaccine compared to free antigen or alum-adjuvanted vaccine.

The antigen used was Staphylococcal Enterotoxin B (SEB) formalinized toxoid F. This antigen was formulated intrinsically in emulsome as described in Example 9, and compared to SEB toxoid-F alone or adjuvanted with alum. BALB/c mice, 5 animals/group, were immunized twice at approximately 3-week intervals by intramuscular injections with 50 μg doses of SEB Toxoid F. Sera, obtained after first and second immunizations, were analyzed by ELISA techniques using anti-SEB as the detecting antibody. As shown in FIG. 5, the intrinsic emulsome formulation was more effective in enhancing immunity to SEB antigens. The anti-SEB serum IgG titers obtained with the emulsome vaccine were higher than those obtained with the alum-adjuvanted formulation or free antigen.

Example 16

ENHANCED LAPINE IMMUNOGENICITY OF SEB TOX-F ANTIGEN AFTER PARENTERAL IMMUNIZATION WITH EXTRINSIC EMULSOME VACCINE COMPARED TO FREE ANTIGEN

Figure 6:
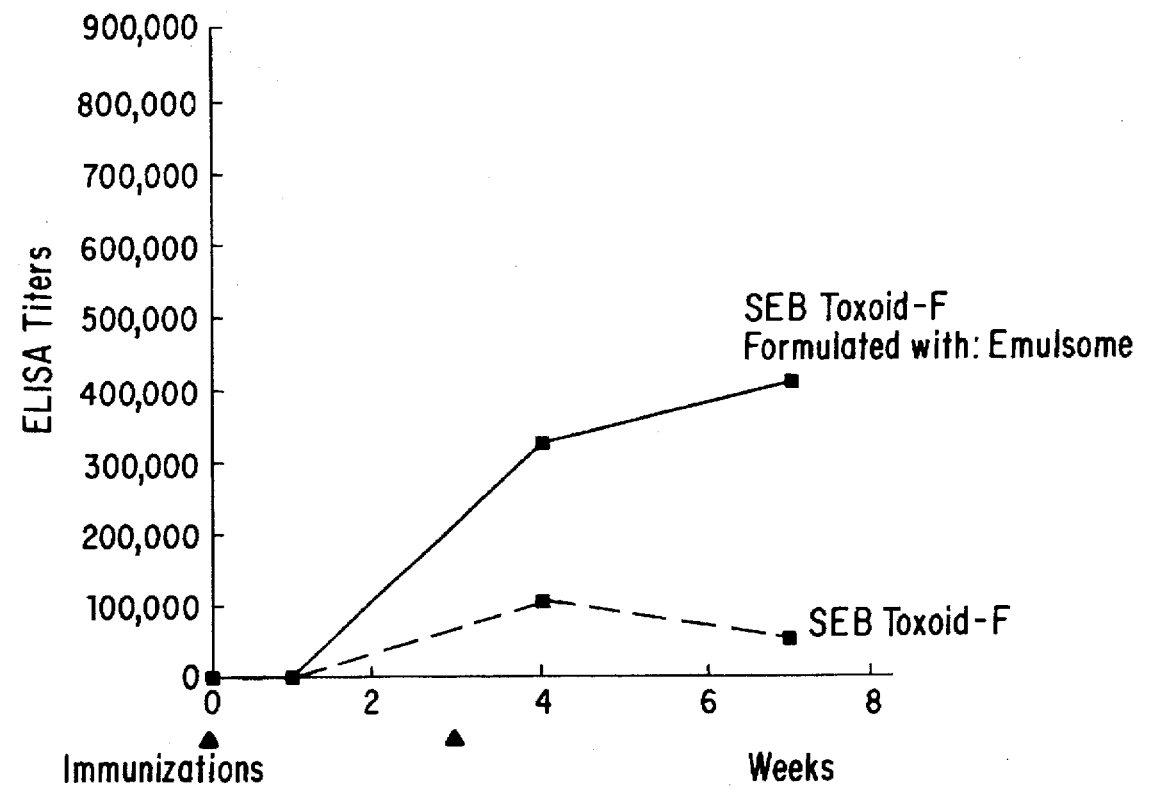

The antigen used was Staphylococcal Enterotoxin B (SEB) formalinized toxoid F. This antigen was formulated extrinsically in emulsomes as described in Example 10, and compared to SEB toxoid-F free antigen. Rabbits, 5 animals/group, were immunized twice at approximately 3 week intervals by intramuscular injections with 100 μg doses of SEB Toxoid F. Sera, obtained after first and second immunizations, were analyzed by ELISA techniques using anti-SEB as the detecting antibody. As shown in FIG. 6, the extrinsic emulsome formulation enhanced 4-fold IgG antibody production compared to the free antigen.

Example 17

PROTECTION AGAINST SYSTEMIC CHALLENGE WITH SEB IN MICE IMMUNIZED PARENTERALLY WITH SEB TOXOID VACCINES FORMULATED WITH ALUM, EMULSOME, OR FREE ANTIGEN

Mice immunized parenterally (Table 3) with Staphylococcus Enterotoxin B in mice immunized with SEB Toxoid-F vaccine formulated with emulsomes (as described in example 9) were significantly protected against systemic SEB challenge (100 ug toxin).

TABLE 3

| Antigen | Formulation | Anti-SEB IgG | Died/total | Survival |
|---------|-------------|--------------|------------|----------|
| control | — | 0 | 9/10 | 10% |
| SEB-tox F | — | 3,200 | 3/5 | 40% |
| SEB-tox F | Alum | 51,200 | 4/5 | 20% |
| SEB-tox F | Emulsome | 102,400 | 0/5 | 100% |

The data in Table 3 show a very good correlation between the anti-SEB serum IgG titers obtained after intramuscular immunization of CD-1 mice with protection against systemic challenge with 100 g of SEB. In the groups immunized with intrinsic emulsome-SEB Toxoid F vaccine, the survival was 100% while for animals immunized with free antigen or alum-adjuvanted vaccine the survival was only 20 to 40%.

Example 18

PROTECTION OF MICE IMMUNIZED WITH MUCOADHESIVE EMULSOME VACCINES CONTAINING SEB-TOXOID F ANTIGEN OR SEB-TOX F COMPLEXED TO PROTEOSOMES AGAINST INTRANASAL CHALLENGE WITH SEB TOXIN IN BALB/C MICE D-GALACTOSAMINE MODEL

Figure 7B:
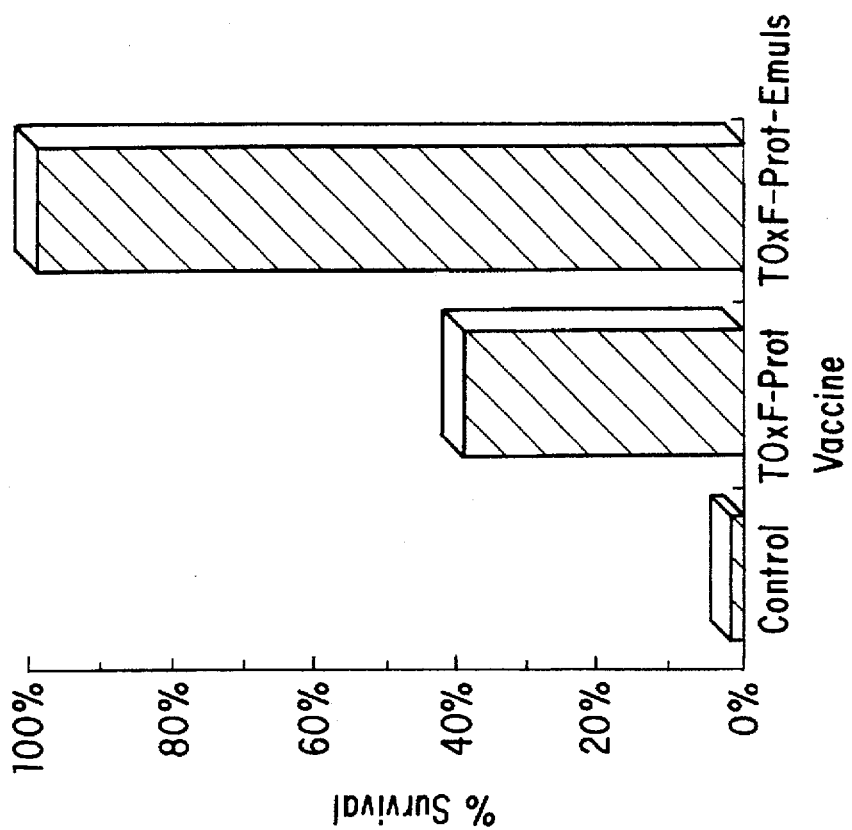
FIGS. 7A and 7B are a pair of graphs showing protection of mice immunized with mucoadhesive emulsome vaccines containing SEB-Toxoid F antigen or SEB-Tox F complexed to proteosomes against intranasal challenge with SEB toxin in BALB/C mice D-galactosamine model.
Figure 7A:
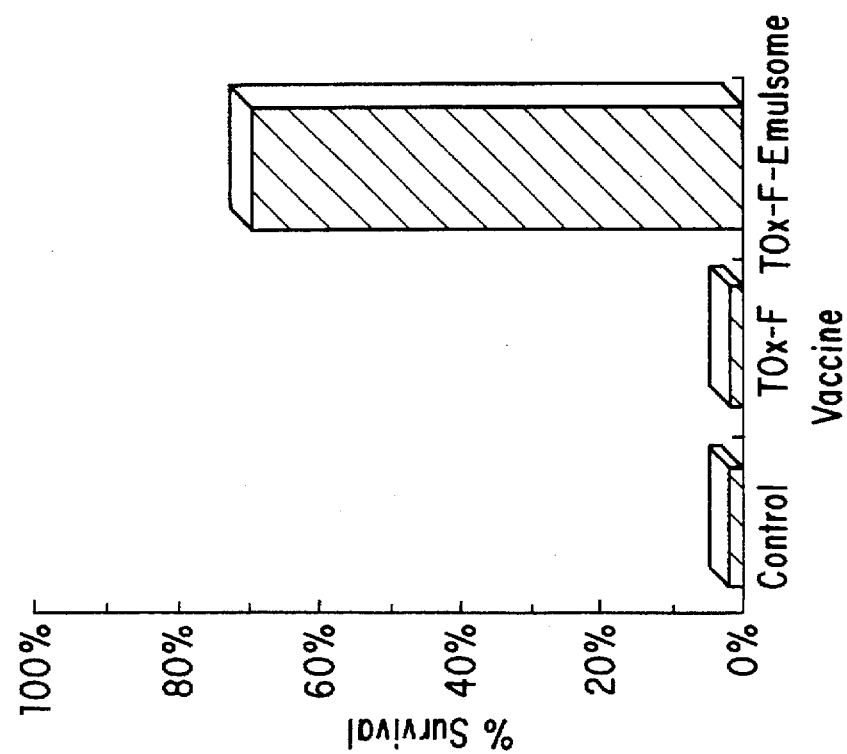

BALB/C mice (10 animals/group) were immunized intranasally twice with 100 μg antigen doses of Mucoadhesive Emulsome vaccines containing either SEB-Tox F antigen or SEB-Tox F complexed to proteosomes. The mucoadhesive formulations were prepared as described in Example 4. The antigens were added extrinsically to the prepared plain emulsomes. After a second immunization mice were challenged intranasally with an LD100 dose (350 μg) of SEB Toxin. Mice survival was determined 3 days post-challenge. FIGS. 7A and 7B clearly show that the mice immunized with the emulsome vaccines had the highest percent of survival either in the Tox F or Tox F complexed to proteosomes groups (70% and 100% survival, respectively,compared to 0 survival in the control group).

Example 19

INDUCTION OF MUCOSAL, INTESTINAL, AND SYSTEMIC IMMUNOGENICITY IN MICE VACCINATED INTRANASALLY WITH ANTI-HIV ENVELOPE gp160 ANTIGEN ALONE OR COMPLEXED TO PROTEOSOMES INCORPORATED IN EXTRINSIC MUCOADHESIVE EMULSOME VACCINES

The antigens used were gp160 alone or gp160 complexed to meningococcal outer membrane proteosomes. These antigens were formulated extrinsically in emulsomes as described in Example 8. Mice (5 animals/group) were immunized intranasally with 100 μg antigen doses at different intervals. Murine sera, lung fluids, and intestinal fluids obtained after immunizations were analyzed by ELISA techniques using several specific HIV epitopes as the detecting antigens.

Table 4 shows that emulsomes enhanced the mucosal immunogenicity of HIV envelope protein following intranasal immunization with HIV gp160 formulated with or without the proteosome vaccine delivery system. Specific systemic anti-HIV IgG antibody production was enhanced 8-fold in the sera of mice immunized with the antigen incorporated in emulsome vaccine formulation, and 128-fold in the sera of mice immunized with the gp160-proteosome-emulsome formulation compared to the free antigen. In addition, immunization with gp160 plus emulsomes without proteosomes enhanced anti-gp160 serum IgA titers of 25,600 compared to <50 obtained by immunizing with the free antigen as well as 270-fold and 6-fold increases in anti-gp160 intestinal and lung fluid IgA, respectively, compared to immunizing with gp160 alone. Table 4 also shows that intranasal immunization with HIV gp160 formulated with emulsomes enhances serum IgG HIV gp41 peptide epitope responses (C448, C41, and CKen) as measured by quantitative western blot analyses. In addition, formulation of the gp160-proteosome vaccine with emulsomes enhances the serum IgG HIV responses to each of seven gp120 and gp41 peptide epitopes tested with increased responses ranging from over 116,000 to 9,000,000.

These data show that optimal antigen delivery to the mucosal immune system is effected by formulating with emulsomes and that specific secretory IgA antibodies can be elicited and boosted even far away from the immunizing site. Lung and intestinal immunity was improved after nasal immunization.

TABLE 4*

| Vaccine Formulation | | | | |
|---|---|---|---|---|
| Anti-gp160 IgG or IgA titers of sera, gavage, and lavage fluids as measured by ELISA: | | | | |
| Anti-gp160 Serum IgG | 51,200 | 409,600 | 1,638,400 | 6,553,600 |
| Anti-gp160 Serum IgA | <50 | <50 | 3200 | 25,600 |
| Anti-gp160 Intestinal IgA | 5 | 147 | 32 | 1351 |
| Anti-gp160 Lung IgA | 512 | 111 | 1176 | 3105 |
| Anti-gp160 peptide igG responses measured by quantitative western blots: | | | | |
| Peptide epitope Specificity: | | | | |
| C1 (48–128) | <100 | <100 | 39,918 | 987,775 |
| C21e (254–274) | <100 | <100 | 7354 | 1,044,098 |
| V3 (290–338) | <100 | <100 | 49,963 | 116,888 |
| C3 (342–405) | <100 | <100 | <100 | 319,355 |
| C448 (453–518) | <100 | 182,362 | <100 | 9,025,282 |
| C41 (579–605) | 210,167 | 1,833,409 | 1,189,986 | 2,469,425 |
| CKen (735–752) | <100 | 73,621 | 15,119 | 2,697,628 |

*Bolded numbers indicate enhancement by emulsomes compared to same vaccine in saline without emulsomes. Underlined numbers indicate enhancement by proteosomes compared to same formulation without proteosomes.

Example 20

INCREASED IMMUNE RESPONSE IN RHESUS MONKEYS IMMUNIZED WITH ANTI-LEISHMANIA INTRINSIC EMULSOME VACCINE CONTAINING LC-467 LIPOPEPTIDE ANTIGEN

Rhesus monkeys (Macacca mulatta, 5 animals/group) were immunized intramuscularly three times at weeks 0, 4 and 10 with 500 μg doses of LC-467 Leishmania lipopeptide antigen incorporated intrinsically in emulsomes as described in Example 13. Monkey sera was collected before and after each immunization and analyzed for anti-Leishmania IgG antibody levels by ELISA.

Figure 8:
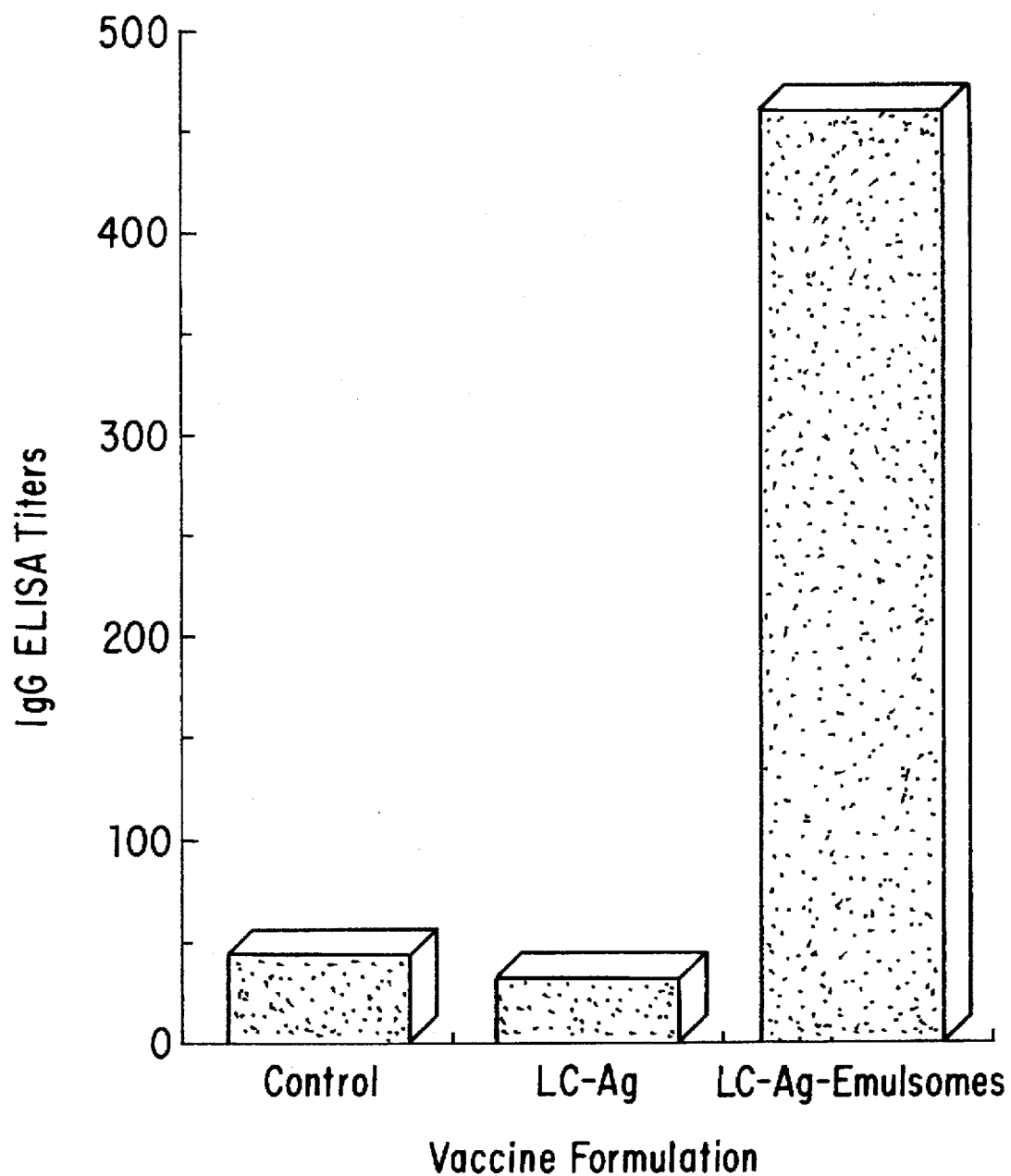
FIG. 8 is a graph showing increased immune response in rhesus monkeys immunized with anti-Leishmania intrinsic emulsome vaccine containing LC-467 lipopeptide antigen.

The results in FIG. 8 show that the monkey group vaccinated with the emulsome vaccine resulted in the highest anti-Leishmania IgG antibody titer, whereas the control group and monkeys that received the LC-467 antigen alone had very low antibody levels.

Example 21

LYOPHILIZATION OF EMULSOMES

To a 0.5 liter round-bottomed flask, 3.5 g of egg-lecithin, 5.2 g of tricaprin, 0.14 g of cholesterol, 0.14 g of cholesterol, 0.14 g of oleic acid, and 0.05 g of tocopherol succinate were added. The lipid mixture was dissolved in 50 ml dichloromethane. The organic solvent was evaporated to complete dryness under reduced pressure using a rotary evaporator (Heidolph, Germany). To the dry lipid film, 63 ml of a 7% sucrose solution were added, and the mixture was then hydrated by shaking until all the lipids were homogeneously dispersed in the aqueous phase. The dispersion was homogenized for 2 minutes at 13,000 rpm using a Polytron PT3000 (Kinematica, AG). The preparation was then submitted to 7 cycles of high shear homogenization at 800 bar using a Microlab70 Gaulin Homogenizer. The formulation was divided in 5 ml portions and the vials were then freeze-dried using a Christ Beta Freeze Dryer (Germany). The samples were reconstituted with water for injection and the particle size distribution of the resultant reconstituted emulsome formulation was measured. An average size of 102±15 was measured, very similar to the mean size obtained before lyophilization.

Example 22

PREPARATION OF POLYMERIC EMULSOMES FOR CONTROLLED RELEASE OF ANTIGENS

To a 0.5 liter round-bottomed flask, 0.5 g of polylactide ("Resomer L 104," MW=2,000 Da, Boehringer Ingelheim, Germany), 0.5 g of egg-lecithin, 0.5 g of tricaprin, 0.2 g of cholesterol, 0.2 g of oleic acid, and 0.02 g of tocopherol succinate were added. The lipid mixture was dissolved in 50 ml dichloromethane. The organic solvent was evaporated until complete dryness under reduced pressure using a rotary evaporator (Heidolph, Germany). To the dry lipid 50 ml of saline were added and the mixture was then hydrated by shaking until all the lipids were homogeneously dispersed in the aqueous phase. The dispersion was homogenized for 5 minutes at 17,000 rpm using a Polytron PT3000 (Kinematica, AG). The preparation was then submitted to 10 cycles of high shear homogenization at 800 bar using a Microlab70 Gaulin Homogenizer. To this emulsome formulation, antigens can be added extrinsically or intrinsically.

The invention has been described with respect to certain specific embodiments thereof. However, those skilled in the art will readily conceive of many other means of carrying out the present invention based upon the generic teachings hereinabove. Applicants propose to be bound, therefore, only by the spirit and scope of the invention as reflected in the appended claims.

What is claimed is:

1. A pharmaceutical composition for the administration of antigen which comprises a nanoemulsion of a plurality of noncellular lipid particles having a mean diameter of about 10 to 250 nm, as determined on a weight basis, the particles being suspended in an aqueous continuous phase, wherein each said lipid particle comprises a lipid core composed of a lipid which is a solid or liquid crystal as determined in bulk at a temperature of about 25° C. or higher, and at least one phospholipid bilayer surrounding said core and encapsulating a portion of said aqueous continuous phase, said particles entrapping about 0.001 to 5% of an immunogen in said lipid core or in said encapsulated aqueous phase.

2. The pharmaceutical composition of claim 1 wherein the mean particle diameter of said lipid particles falls within the range of about 20 to 180 nm as determined on a weight basis.

3. The pharmaceutical composition of claim 2 wherein the particle diameter of at least 99% of said lipid particles falls within the range of about 50 to 150 nm as determined on a weight basis.

4. The pharmaceutical composition of claim 2 wherein the lipid core comprises a fatty acid ester.

5. The pharmaceutical composition of claim 4 wherein the lipid core has a solid to fluid phase transition temperature below 37° C. as determined in bulk.

6. The pharmaceutical composition of claim 4 wherein the lipid core comprises a triglyceride.

7. The pharmaceutical composition of claim 6 wherein said triglyceride comprises a fatty acid moiety of $C_{10}$ to $C_{18}$.

8. The pharmaceutical composition of claim 6 wherein said triglyceride is completely saturated.

9. The pharmaceutical composition of claim 6 wherein said triglyceride is selected from the group consisting of tricaprin, trilaurin, trimyristin, tripalmitin, and tristearin.

10. The pharmaceutical composition of claim 6 wherein the mole ratio of phospholipid to total lipid is in the range of from 0.1:1 to 0.5:1.

11. The pharmaceutical composition of claim 6 wherein the weight ratio of phospholipid to triglyceride is in the range of from 0.5:1 to 1.5:1.

12. The pharmaceutical composition of claim 4 wherein said phospholipid is a phosphatidylcholine.

13. The pharmaceutical composition of claim 12 wherein said phosphatidylcholine is egg phosphatidylcholine.

14. The pharmaceutical composition of claim 12 wherein said phosphatidylcholine has a transition temperature below 25° C.

15. The pharmaceutical composition of claim 12 wherein said phosphatidylcholine is saturated.

16. The pharmaceutical composition of claim 1 wherein said lipid particle contains cholesterol or cholesteryl esters.

17. The composition of claim 1 wherein the immunogen is hydrophilic, lipophilic, or amphophilic.

18. The composition of claim 1 wherein the immunogen is a peptide, protein, or glycoprotein.

19. The composition of claim 18 wherein the antigen is the gp160 envelope protein of the HIV virus, or a fragment thereof.

20. The composition of claim 18 wherein the antigen is the surface glycoprotein of a Leishmania parasite, or a fragment thereof.

21. The composition of claim 20 wherein the surface glycoprotein or peptide is covalently conjugated to a hydrophobic component.

22. The composition of claim 21 wherein the hydrophobic component is lauryl-cysteine.

23. The composition of claim 1 wherein the immunogen is a protein toxoid.

24. The composition of claim 23 wherein the immunogen is *Staphylococcus Enterotoxin* B toxoid.

25. The composition of claim 1 wherein the immunogen is complexed with a proteosome.

26. The composition of claim 1 wherein the nanoemulsion further comprises a bioadhesive or mucoadhesive macromolecule.

27. The composition of claim 26 wherein the said mucoadhesive macromolecule is a polymer.

28. The composition of claim 26 wherein the said mucoadhesive macromolecule is selected from the group of acidic nonnatural polymers consisting of polymers and copolymers containing acrylic acid units, polymers and copolymers containing methacrylic acid units, and poly (methylvinylether/maleic anhydride) copolymer.

29. The composition of claim 28 wherein the said polymer is polyacrylic acid.

30. The composition of claim 1 which contains no added muramyl peptides.

31. The pharmaceutical composition of claim 1 wherein said lipid particle is substantially free of lipase and phospholipase activity.

32. A method for delivery of an immunogen to an animal, comprising administering to said animal a pharmaceutical according to claim 1.

33. The method of claim 32 wherein the mean diameter of the lipid particles in said composition is in the range of about 20 to 180 nm.

34. The method of claim 32 wherein said composition is administered parenterally, orally, intranasally, or topically, thereby providing enhanced immunogenicity.

35. The method of claim 32 wherein said composition is administered to mucosal surfaces, thereby achieving mucosal immunity.

36. A method for making a nanoemulsion for administration of an immunogen, comprising the steps of:

preparing a mixture comprising phospholipid and triglyceride in the weight ratio range of about 0.5:1 to 1.5:1 wherein said triglyceride has a solid to liquid phase transition temperature of greater than 25° C.;

suspending said mixture in an aqueous solution at a temperature below the solid to liquid transition temperature of the triglyceride;

reducing the size of the suspension to yield a nanoemulsion of lipid particles having a mean particle diameter of between about 10 nm and 250 nm; and incorporating an immunogen in the nanoemulsion.

37. The method according to claim 36 for preparing the composition of the nanoemulsion by an intrinsic procedure, where the immunogen is added before homogenization of water and oil phases.

38. The method of claim 36 for preparing the composition of the nanoemulsion by an extrinsic procedure, where the immunogen is added externally by mixing with the previously prepared plain nanoemulsion.

39. A pharmaceutical composition comprising dehydrated lipid particles containing an antigen for administration as a nanoemulsion, wherein said lipid particles comprise a lipid core surrounded by at least one phospholipid layer, said lipid core is composed of lipid in a solid or liquid crystalline phase at least about 25° C. as determined in bulk, and said lipid particles have a mean diameter upon rehydration of about 10 to 250 nm.

40. The pharmaceutical composition of claim 39 further comprising a cryoprotectant.

41. The pharmaceutical composition of claim 40 wherein said cryoprotectant is selected from the group consisting of glucose, sucrose, lactose, maltose, trehalose, dextran, dextrin, cyclodextrin, polyvinylpyrrolidone, and amino acids.

42. The pharmaceutical composition of claim 40 wherein said cryoprotectant is present in a range of from 0.1% to 10% by weight compared to lipid.

43. The pharmaceutical composition of claim 39 wherein said lipid particles contain an immunogen.

44. A method for delivering an antigen to an animal comprising administering to said animal a pharmaceutical composition according to claim 39.

* * * * *